United States Patent [19]

Giger et al.

[11] Patent Number: 5,133,020

[45] Date of Patent: Jul. 21, 1992

[54] AUTOMATED METHOD AND SYSTEM FOR THE DETECTION AND CLASSIFICATION OF ABNORMAL LESIONS AND PARENCHYMAL DISTORTIONS IN DIGITAL MEDICAL IMAGES

[75] Inventors: Maryellen L. Giger, Elmhurst; Kunio Doi, Hinsdale; Charles E. Metz, Willowbrook; Fang-Fang Yin, Chicago, all of Ill.

[73] Assignee: Arch Development Corporation, Chicago, Ill.

[21] Appl. No.: 383,097

[22] Filed: Jul. 21, 1989

[51] Int. Cl.$^5$ ............................................. G06K 9/00
[52] U.S. Cl. ................................... 382/6; 364/413.23; 382/18
[58] Field of Search ............................. 382/6, 18, 51; 364/413.19, 413.17, 413.23, 413.13

[56] References Cited

U.S. PATENT DOCUMENTS

| | | | |
|---|---|---|---|
| 4,217,641 | 8/1980 | Naparstek | 382/6 |
| 4,335,427 | 6/1982 | Hunt et al. | 382/6 |
| 4,635,293 | 1/1987 | Watanabe | 382/6 |
| 4,907,156 | 3/1990 | Doi et al. | 364/413.13 |

OTHER PUBLICATIONS

Rafael C. Gonzalez; "Digital Image Processing"; 1977, Addison-Wesley Publishing Co. pp. 126-137.

Ernest L. Hall; "Computer Image Processing and Recognition"; 1979, Academic Press, pp. 172-181.

Primary Examiner—Leo H. Boudreau
Attorney, Agent, or Firm—Oblon, Spivak, McClelland, Maier & Neustadt

[57] ABSTRACT

A method for automated analysis of abnormalities in the form of lesions and parenchymal distortions using digital images, including generating image data from respective of digital images derived from at least one selected portion of an object, for example, from mammographical digital images of the left and right breasts. The image data from each of the digital images are then correlated to produce correlated data in which normal anatomical structured background is removed. The correlated data is then searched using one or more predetermined criteria to identify in at least one of the digital images an abnormal region represented by a portion of the correlated data which meets the predetermined criteria. The location of the abnormal region is then indicated, and the indicated location is then subjected to classification processing to determine whether or not the abnormal region is benign or malignant. Classification is performed based on the degree of spiculations of the identified abnormal region. In order to enhance the process of searching for abnormal regions, in one embodiment the gray-level frequency-distributions of two or more images are matched by matching the cumulative gray-level histograms of the images in question.

108 Claims, 23 Drawing Sheets

IMAGE 1

IMAGE 2

IMAGE 3

IMAGE 4

IMAGE 5

IMAGE 6

IMAGE 7

IMAGE 8

IMAGE 9

IMAGE 10

— LEFT BREAST
----- RIGHT BREAST

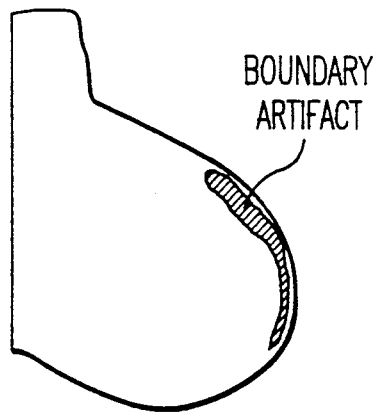
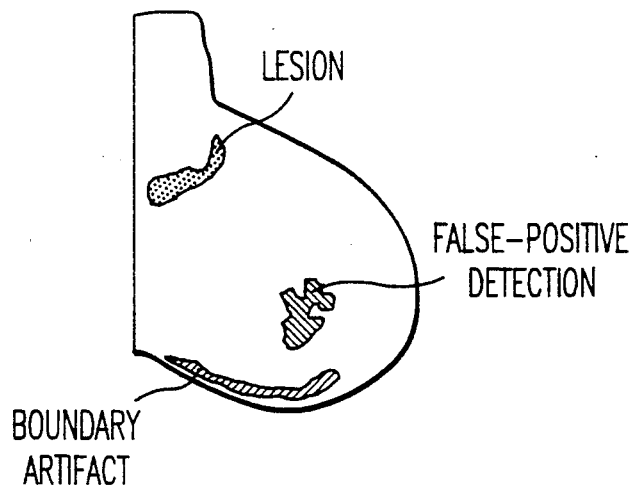
FIG. 14(a)  FIG. 14(b)
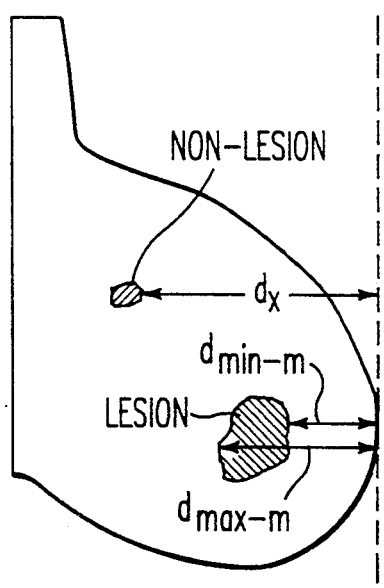
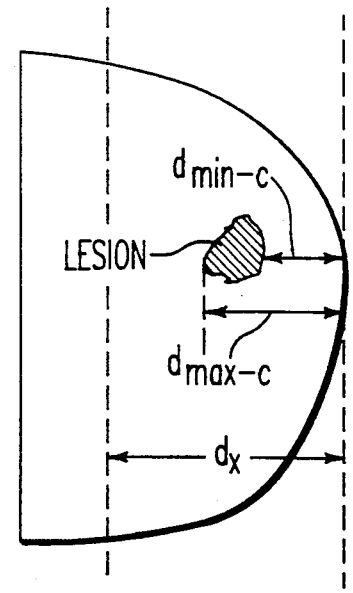
FIG. 15(a)  FIG. 15(b)

AUTOMATED METHOD AND SYSTEM FOR THE DETECTION AND CLASSIFICATION OF ABNORMAL LESIONS AND PARENCHYMAL DISTORTIONS IN DIGITAL MEDICAL IMAGES

The present invention was made in part with U.S. Government support under grant number 2 RO1 CA24806-11 from the Department of Health and Human Services and the National Cancer Institute. The U.S. Government has certain rights in the invention.

BACKGROUND OF THE INVENTION

1. Field of the Invention:

This invention relates generally to a method and system for automated processing of medical images using feature-extraction techniques, and more particularly, to an automated method and system for the detection and classification of abnormal regions in digital medical images.

2. Discussion of the Background:

Detection and classification of abnormal lesions and distortions in radiographs, such as masses and parenchymal distortions in breast radiographs, so called mammograms, are among the most important and difficult tasks performed by radiologists.

Breast cancer is the most common malignancy occurring in women and its incidence is rising. Breast cancer will occur in approximately one out of every ten women sometime during their lifetime. At present, mammography is the most effective method for the early detection of breast cancer. Studies indicate that 26% of nonpalpable cancers present mammographically as a mass while 18% present both with a mass and microcalcifications. Thus, many breast cancers are detected and referred for surgical biopsy on the basis of a radiographically detected mass lesion.

Visual characteristics currently used by radiologists to distinguish between malignant and benign lesions include analysis of the contour of the mass, the degree of associated parenchymal retraction and distortion, and the density of the mass. Although general rules for the differentiation between benign and malignant breast lesions exist, considerable error in the classification of lesions occurs with the current methods of radiographic characterization. In fact, on average, only 10-20% of masses referred for surgical breast biopsy are actually malignant.

Surgical biopsy is an invasive technique that is an expensive and traumatic experience for the patient and leaves physical scars that may hinder later diagnoses (to the extent of requiring repeat biopsies for a radiographic tumor-simulating scar). In addition, the miss rate for the radiographic detection of malignant lesions ranges from 12 to 30 percent. A computer scheme capable of detecting and analyzing the characteristics of benign and malignant lesions and parenchymal distortions, in an objective manner, should aid radiologists by reducing the numbers of false-negative and false-positive diagnoses of malignancies, thereby decreasing patient morbidity as well as the number of surgical biopsies performed and their associated complications.

Long term studies of patients have shown that prognosis of breast cancer depends on the size of the tumor at the onset of treatment. Various studies have indicated that regular mammographic screening can reduce the mortality from breast cancer in women. The American Cancer Society has strongly recommended the use of mammography for the early detection of breast cancer. Their present recommendations include obtaining a baseline mammogram on all asymptomatic women over the age of 35 followed by biannular examinations between the ages of 40 and 49, with annular examinations after the age of 50. Thus, mammography may become one of the largest volume X-ray procedures routinely interpreted by radiologists. It is apparent that the efficiency and effectiveness of screening procedures could be increased substantially by use of a computer system that successfully aids the radiologist in detecting lesions and making diagnostic decisions.

Several investigators have attempted to analyze mammographic abnormalities with computers (See Winsberg et al, Radiology 89: 211-215, 1967; Ackerman et al., Cancer 30: 1025-1035, 1932; Ackerman et al., Cancer 31: 342-352, 1973; Fox et al., Proc. IEEE, 5th International Conference on Pattern Recognition: 624-631, 1980; and Magnin et al., Optical Engineers, 25: 780-784, 1986). Of those attempted, feature-extraction techniques were used without utilizing the bilateral symmetry information of the left and right mammograms. In addition, the spatial frequency characteristics of the spiculations of suspected lesions were not considered. Basically, the known earlier studies failed to achieve an accuracy acceptable for clinical practice. Chan. et al, Proc. SPIE 767: 367-370, 1987 have reported that successful attempts have been made in the detection of microcalcifications in digital mammograms (but not for lesions and parenchymal distortions).

SUMMARY OF THE INVENTION

Accordingly, an object of this invention is to provide an automated method and system for detecting, classifying and displaying abnormal lesions and parenchymal distortions existing in a digital medical image.

Another object of this invention is to provide an automated method and system for providing reliable early diagnosis of abnormal anatomic lesions and parenchymal distortions.

A further object of this invention is to provide an automated method and system for selecting and displaying abnormal lesions and parenchymal distortions by correlating structured anatomic background between two or more images of the same object (i.e., anatomical part) or mirrored counterparts (i.e., left and right breasts, lungs, kidneys etc.) before applying feature-extraction techniques.

A further object of this invention is to provide a method and system for matching the gray-level frequency-distributions of two or more images by matching the cumulative gray-level histograms of the images in question.

A further object of this invention is to provide an automated method and system for classifying and displaying abnormal lesions and parenchymal distortions by frequency analysis of the borders of the suspected lesions and parenchymal distortions.

These and other objects are achieved according to the invention by providing a new and improved automated method and system in which prior to feature extraction, correlation of two or more images of the same body part (e.g., different with respect to time or projection view) or its mirrored counterpart (e.g., left and right anatomic parts) is performed. For example, the correlation of the mammograms of the left and right breasts, images of the left and right hands, images of the left and right kidneys or mammograms obtained at different views or different times is performed. Then, according to the invention, comparison data is obtained through correlation of the images to remove normal anatomic background common to both.

Further according to the invention, once the structured background is removed, feature extraction, based on for example thresholding, size and relationships to other anatomic structures and/or images, is performed. Threshold levels are varied to test for the probability of the presence of a lesion or parenchymal distortion. Relationships to other images involving multiple views of the two images, such as the cranio-caudal view and the medial-lateral view of both the left and right breast in mammography, are used.

Further according to the invention, once a lesion or parenchymal distortion is detected, frequency analysis of its borders is performed to determine the degree of malignancy. Differences between the detected lesion or distortion and a smooth version are determined in order to determine the fluctuations of the border, such as the spiculations on a mammographic mass.

BRIEF DESCRIPTION OF THE DRAWINGS

A more complete appreciation of the invention and many of the attendant advantages thereof will be readily obtained as the same becomes better understood by the reference to the following detailed description when considered in connection with the accompanying drawings, wherein:

FIGS. 14(a) and 14(b) are illustrations of possible artifacts arising from imperfect overlap of the breast boundaries indicated in FIG. 13;

FIGS. 15(a) and 15(b) are illustrations describing the workings of the correlation test to remove false-positive detections;

DETAILED DESCRIPTION OF THE PREFERRED EMBODIMENTS

Figure 1:
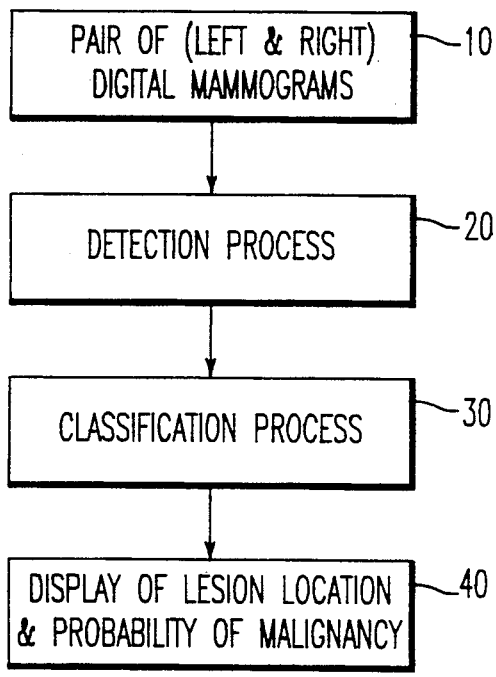
FIG. 1 is a schematic diagram illustrating the automated method for lesion and parenchymal distortion detection and classification according to the invention.

Referring now to the drawings, and more particularly to FIG. 1 thereof, a schematic diagram of the lesion and parenchymal distortion detection and classification scheme is shown. The overall scheme includes an initial acquisition of at least a pair of digital mammograms (step 10), and both a detection process (step 20) and a classification process (step 30), each to be described separately. The output of the detection part can serve as the input to the classification part. The final outcome of the overall scheme is the display of the suspect lesion location and its corresponding probability of malignancy (step 40).

Figure 2:
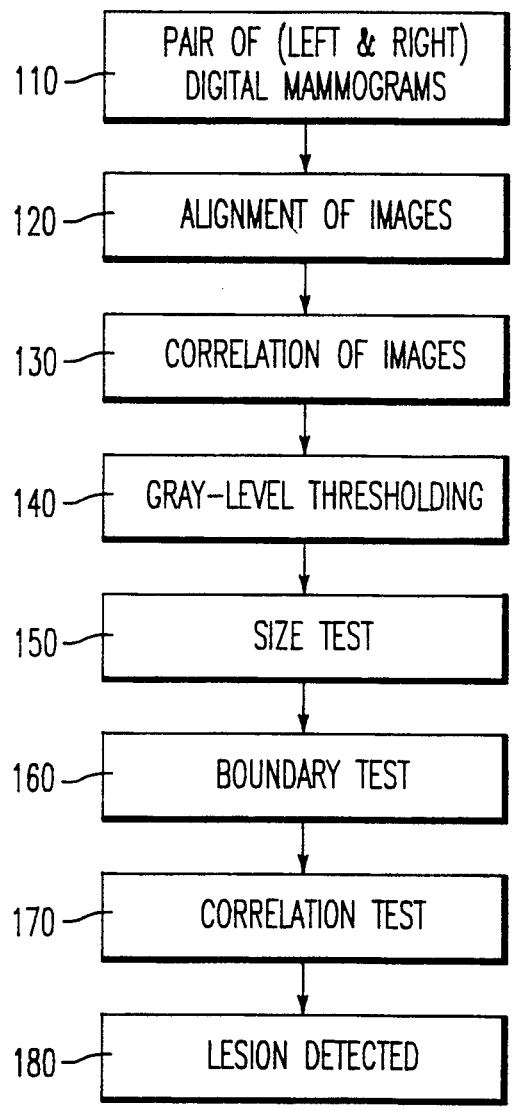
FIG. 2 is a detailed schematic diagram illustrating the automated method for lesion and parenchymal distortion detection alone according to the invention.

FIG. 2 shows a schematic diagram of the detection process. The technique begins with an attempt to increase the conspicuity of the lesion or distortion by correlating the normal anatomic background, particular to the patient in question, in two or more images. In mammography this involves a bilateral correlation technique using the architectural symmetry of the left and right breasts. Other applications, involving the correlation of anatomic background in two or more images, include the use of multiple views of the left and right breasts (e.g., cranio-caudal and medio-lateral) combined with the bilateral architectural symmetry of the two breasts. Also, multiple images can be correlated with respect to time to distinguish variations in the detected lesion in order to establish growth patterns of the lesion that are related to malignancy. For example, lesions that do not change for years are usually considered to be benign.

In mammography, the correlation technique is accomplished by initially obtaining digital images (step 110) of the left and right breasts at the same view (e.g., craniocaudal). Next the breast image in each of the digital images are aligned spatially to each other. This alignment can be performed at the time of digitization when a TV camera digitizer is used, which enables manual positioning of the images, real time viewing of the digital image and real time subtraction of two or more images in order to check the boundary alignment. The alignment can also be performed after digitization using image processing techniques such as translation, rotation and/or warping (See Hall, Computer Image Processing and Recognition (Academic Press, 1979)) of the boundary of each breast (step 120). Next the correlation of the multiple-image data is performed (step 130).

Figure 3:
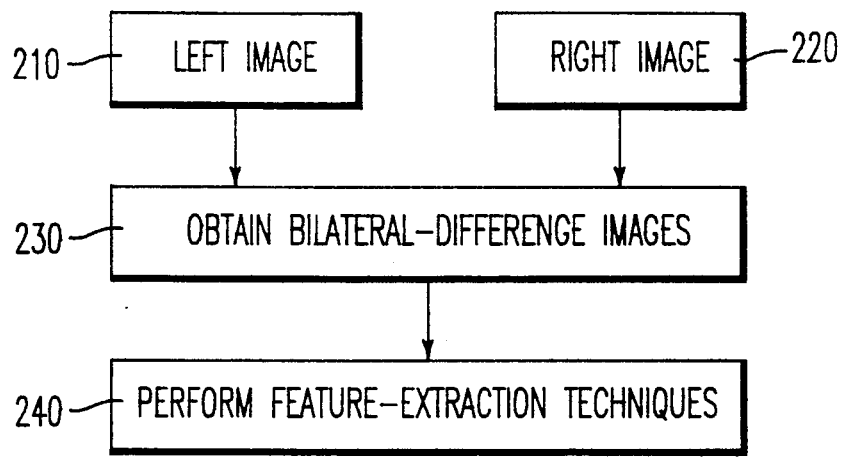
FIG. 3 is a schematic diagram illustrating a method for correlating the multiple-image data (Method 1)

A simple subtraction (method 1) of the left and right images is shown in FIG. 3. However, artifacts may be introduced due to possible variations in exposure conditions that may produce global gray-level variations, and so also examined and described are three other correlation techniques (using a "left-minus-right" convention) that correlate the normal anatomic background between each breast image prior to the application of various feature-extraction techniques. In method 1 (FIG. 3), the right image (220) is subtracted from the left image (210) after alignment of the breast boundaries, in order to obtain a bilateral-difference image (step 230). Feature-extraction techniques (step 240) are then performed to isolate suspect lesions from normal anatomic background.

Figure 4:
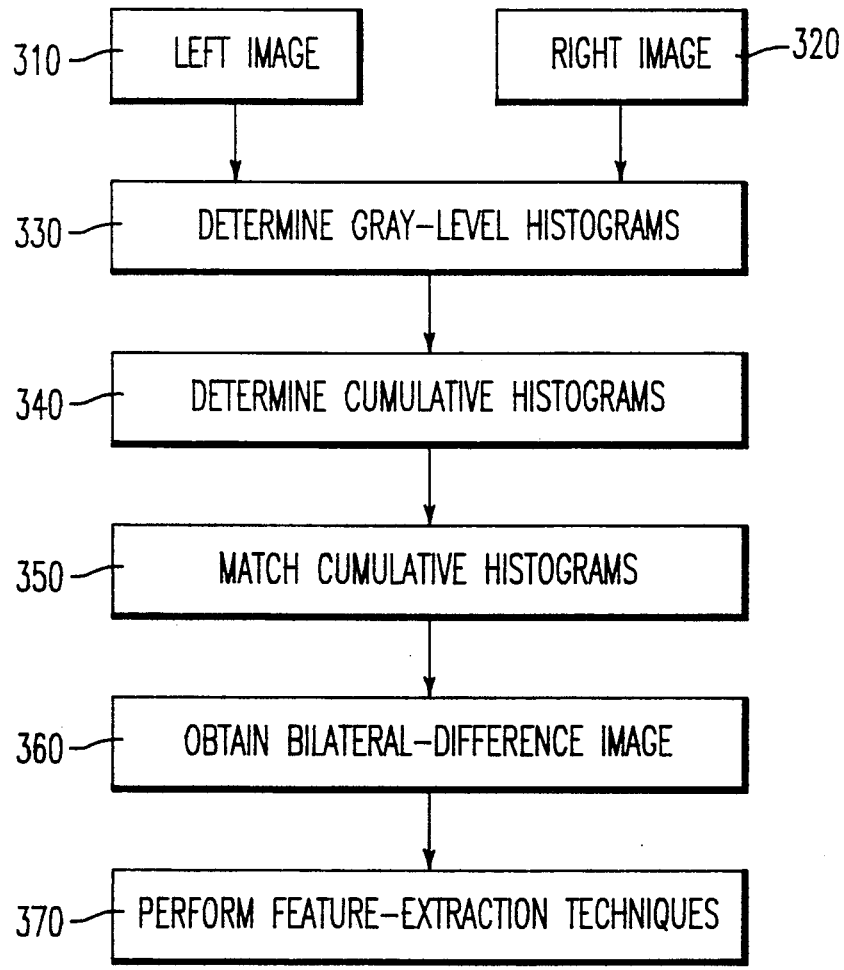
FIG. 4 is a schematic diagram illustrating another method for correlating the multiple-image data (Method 2)

In method 2 (FIG. 4), the gray-level frequency distributions of the left and right breast images are matched (by matching the cumulative gray-level histograms of the two images) prior to subtraction in an attempt to match the densities of the normal breast architecture. Initially, the gray-level histograms of the left image (310) and the right image (320) are determined (step 330). From each of the gray-level histograms, the cumulative histogram is determined (step 340).

Figure 5:
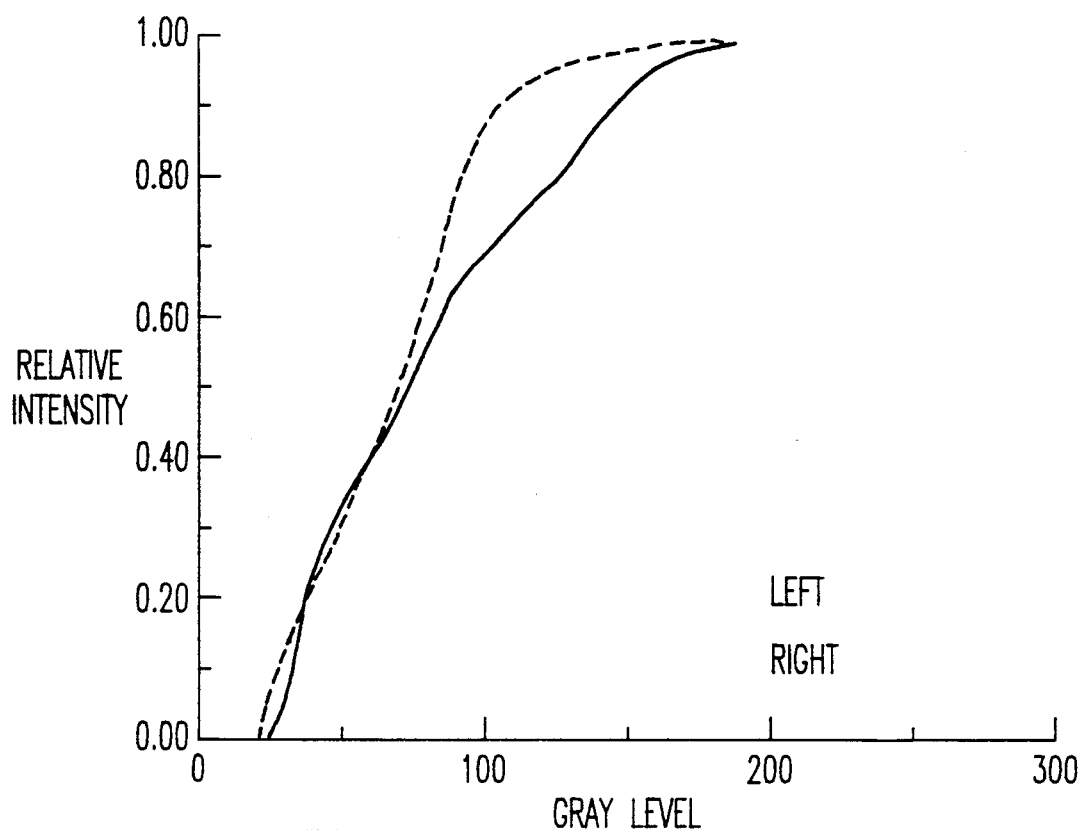
FIG. 5 is a graph illustrating the cumulative histograms of a left mammogram and a right mammogram.

FIG. 5 illustrates the cumulative histograms of two corresponding left and right mammograms prior to such matching. For each gray level in the right mammogram, a conversion (in terms of gray levels) is determined, as illustrated by the arrow in FIG. 5. For example, modification of the gray levels in the right image (in order to match the cumulative histogram of the left image) involves the conversion of all pixels having a gray level of 100 to a gray level of 142. Similar conversions, relating the values of the cumulative histograms, are determined for each gray level. Gray-level conversion of the pixel values of the right mammogram is then performed using this relationship in order to match the cumulative histogram of the right breast image to that of the left breast image (step 350). The difference of one of the original images (e.g., the left mammogram) and a gray-level modified version of the other original image (e.g., the right mammogram) is then obtained (step 360). Gray-level thresholding is performed on the difference image to extract possible lesions, and these suspected lesions are then subjected to various feature-extraction techniques (to be discussed later) (step 370).

It should be noted that when more than two images are used, such as when multiple images are obtained over a given period of time, the gray-level frequency distributions of all the images can be matched to a selected one of the images. Such matching is useful, for example, in order to reduce variations between the images caused by variations in the acquisition and/or exposure conditions employed. Correlation of such multiple image data can then be accomplished by determining the maximum gray level over all values with respect to time at each pixel location and determining the minimum gray level at each pixel location. Comparison of such data yields information on the growth of the lesion with respect to time.

It should be noted that this technique of matching the cumulative gray-level histograms of two or more images can be applied, in general, in many applications such as image processing for human vision and/or computer vision. For example, images from multiple CT (computed tomography) slices or images obtained at different times could be matched with respect to density using this technique.

In methods 3 (FIG. 6) and 4 (FIG. 7), bilateral subtraction is performed after gray-level thresholding of the individual original images. This gray-level thresholding can be performed with or without prior application of cumulative histogram matching (described earlier). Gray-level thresholding is performed on each of the two images at specified levels (e.g., at ten different threshold levels).

Figure 6:
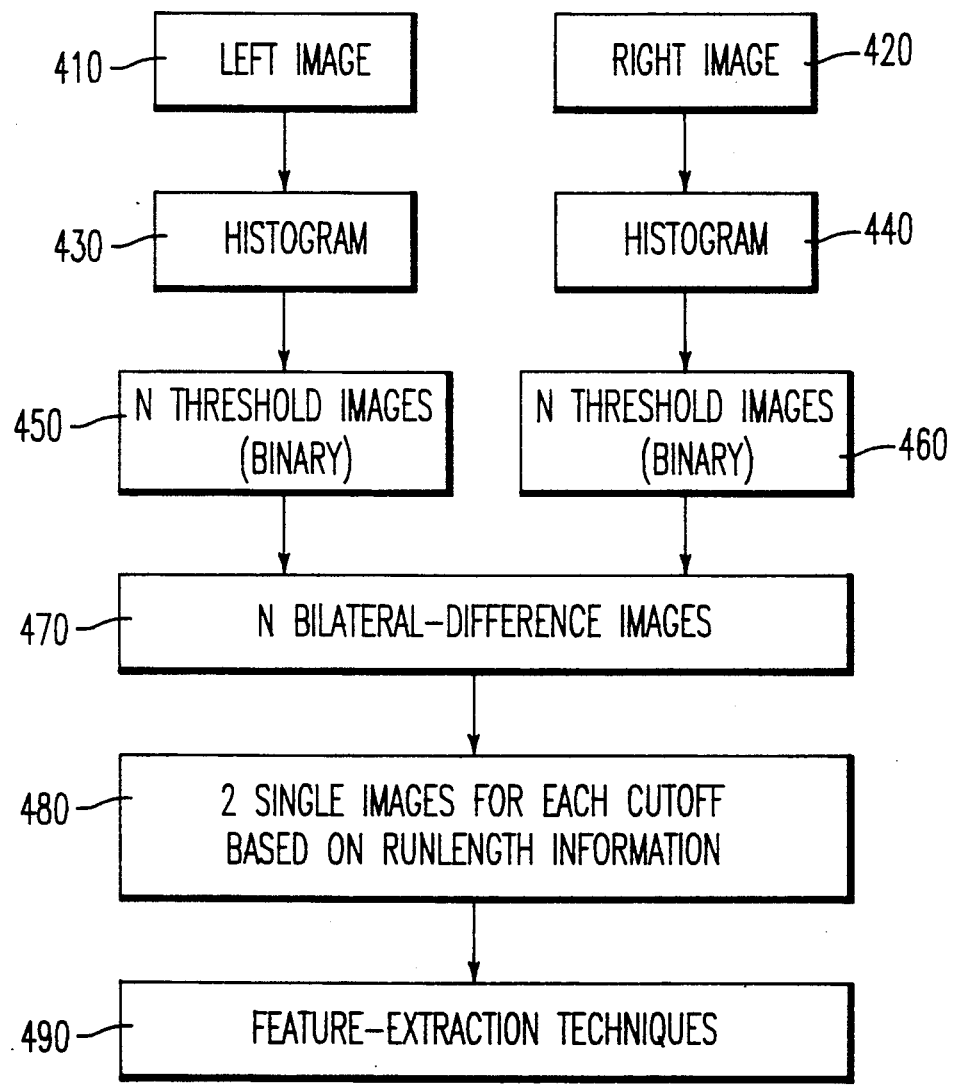
FIG. 6 is a schematic diagram illustrating another method for correlating the multiple-image data (Method 3)
Figure 7:
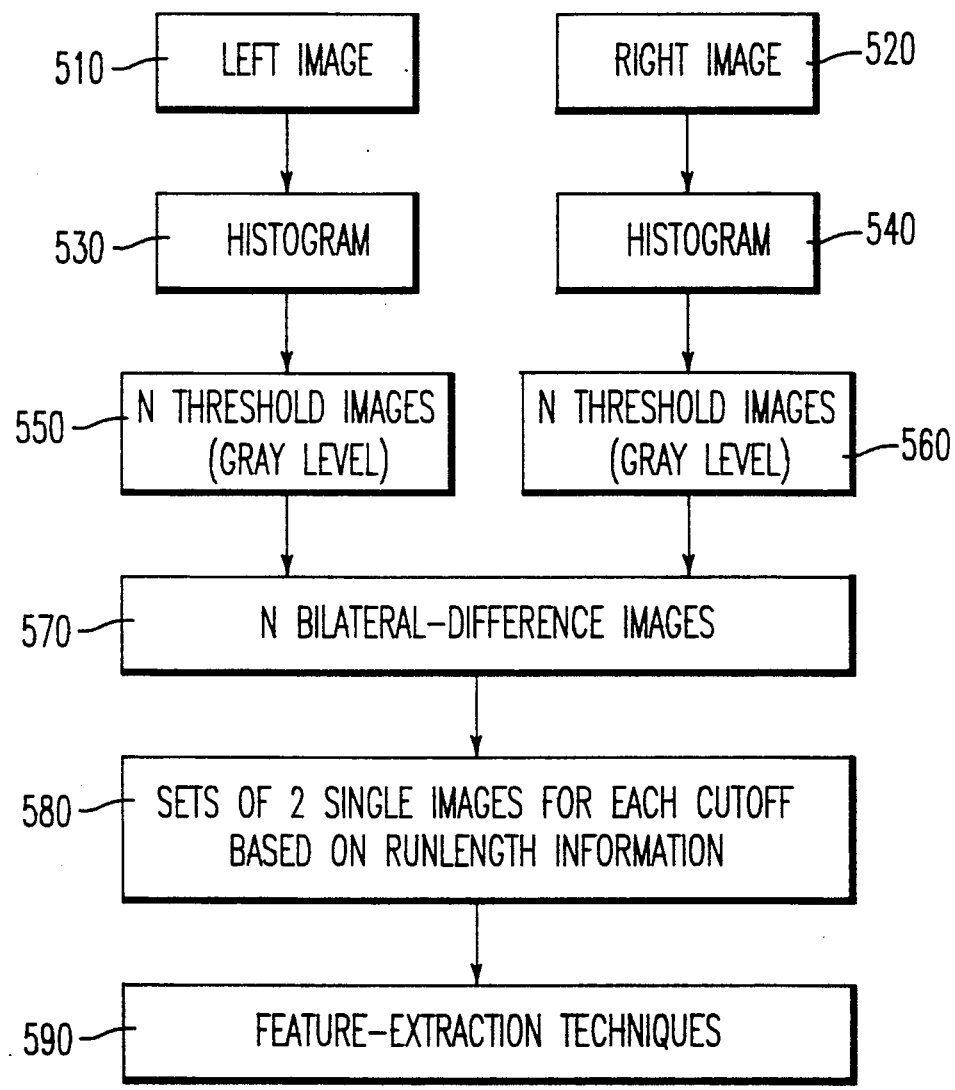
FIG. 7 is a schematic diagram illustrating another method for correlating the multiple-image data (Method 4)
Figure 8A:
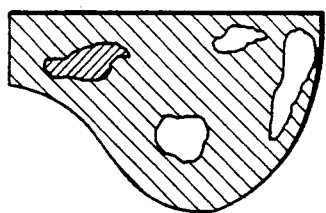
FIGS. 8(a)-8(f) are illustrations demonstrating the bilateral-difference images used in method 3.
Figure 8B:
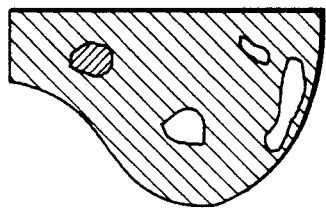
Figure 8C:
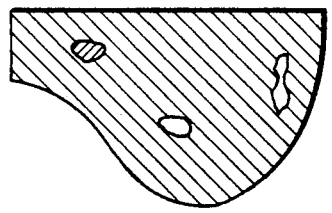
Figure 8D:
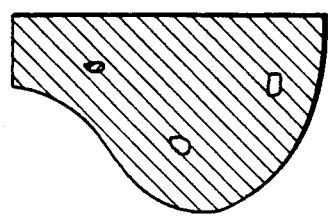
Figure 8E:
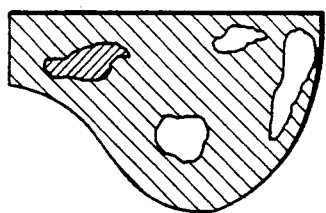
Figure 8F:
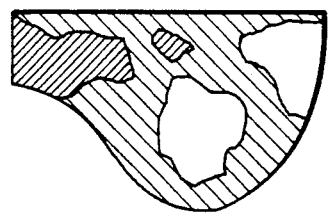
Figure 8G:
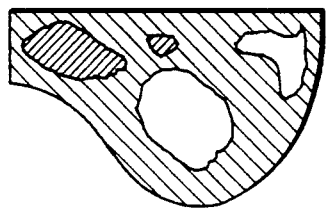
Figure 8H:
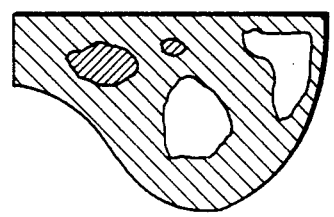
Figure 8I:
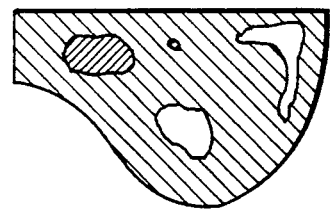
Figure 8J:
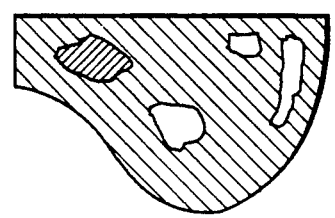

In methods 3 (FIG. 6) and 4 (FIG. 7), left and right image data are obtained for the left and right breasts (Steps 410, 420—FIG. 6; Steps 510, 520—FIG. 7). Gray-level histograms are then obtained for each image (Steps 430, 440—FIG. 6; Steps 530, 540—FIG. 7). These histograms are determined to obtain N threshold values against which each pixel of the left and right images originally obtained will be compared. Each threshold value is chosen at a level corresponding to a specific percentage (e.g., each 10%) of the area under the gray-level histogram of each image. Once the gray-level threshold values are obtained from the histograms of the left and right images, the data values of each pixel of the left and right images are compared with each of the N threshold values to determine N threshold images, one for each threshold value (steps 450, 460; steps 550, 560). In steps 450, 460 of method 3, pixel values below a given threshold are set to a constant value and pixel values equal to or above the given threshold value are given another constant value. In steps 550, 560 of method 4, pixel values below a given threshold value are likewise assigned a constant value, whereas pixel values above the given threshold remain unchanged. Upon completion of steps 450, 460 (method 3) and steps 550, 560 (method 4) there are obtained N threshold images, one for each of the N threshold values determined from the gray-level histograms of each left and right image, with the value of each pixel of each of the N threshold images in method 3 having a binary value, and in method 4 having a constant value for original image data values below the given gray-level thresholds and an unchanged value for original image data values above the given gray-level threshold. Then in both methods 3 and 4, N bilateral difference images are determined from each pair of threshold images derived by thresholding at the same threshold value using the "left minus right" convention (steps 470; 570).

FIG. 8 illustrates schematically 10 bilateral-difference images obtained with method 3. Since normal breast architecture will be similar in the left and right breasts, the majority of such similar regions will either be below the gray-level cutoff during a particular thresholding or be at a similar gray level percentage, and thus be eliminated in the production of the bilateral difference images. It should be noted that large positive and negative values correspond to possible lesions in the left and right breasts, respectively, due to the "left-minus-right" convention.

Figure 9A:
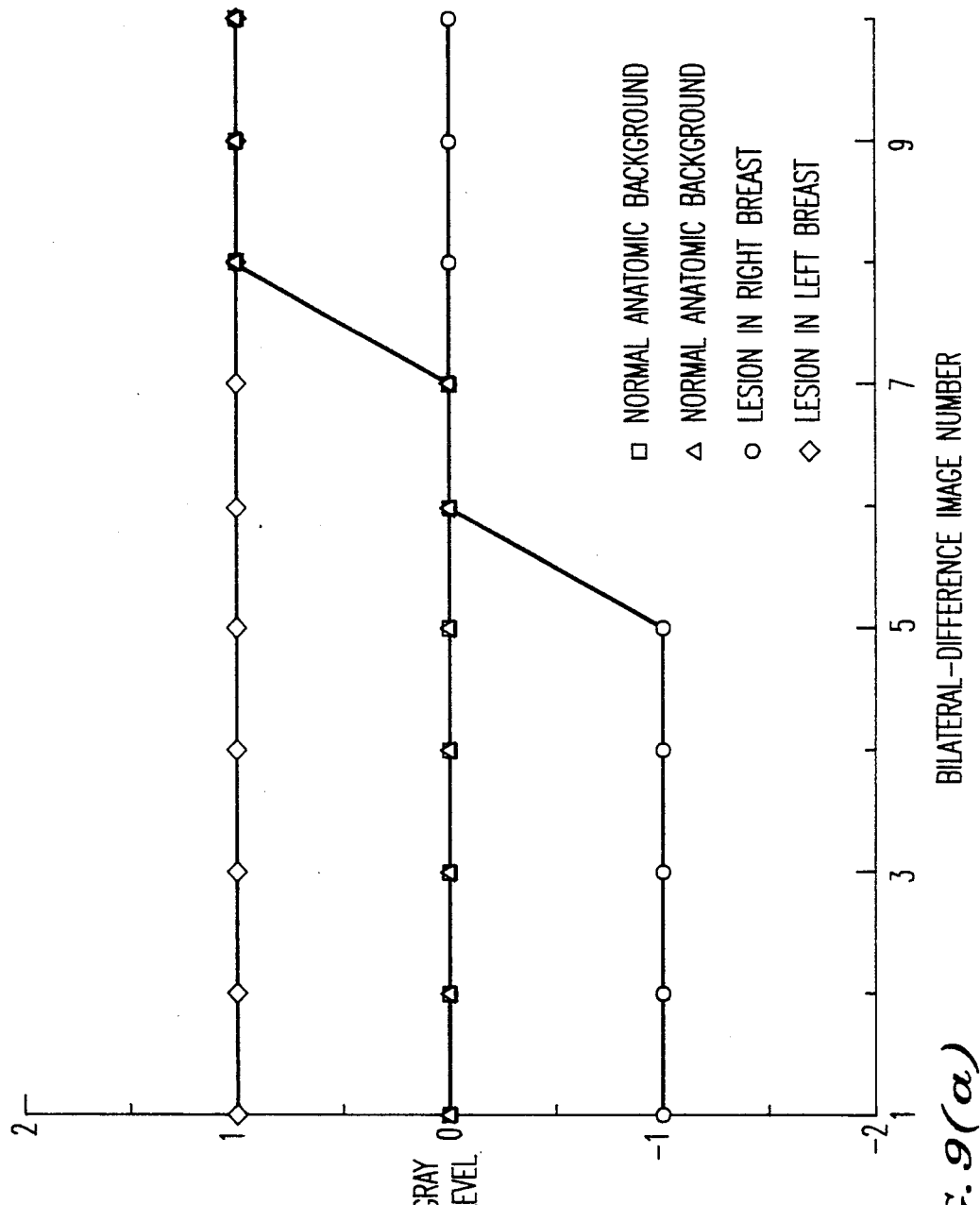
FIG. 9(a) and 9(b) are illustrations of the changes in gray level in the difference images for a normal breast area, a lesion in a left breast and a lesion in a right breast as obtained for method 3 and method 4, respectively.
Figure 9B:
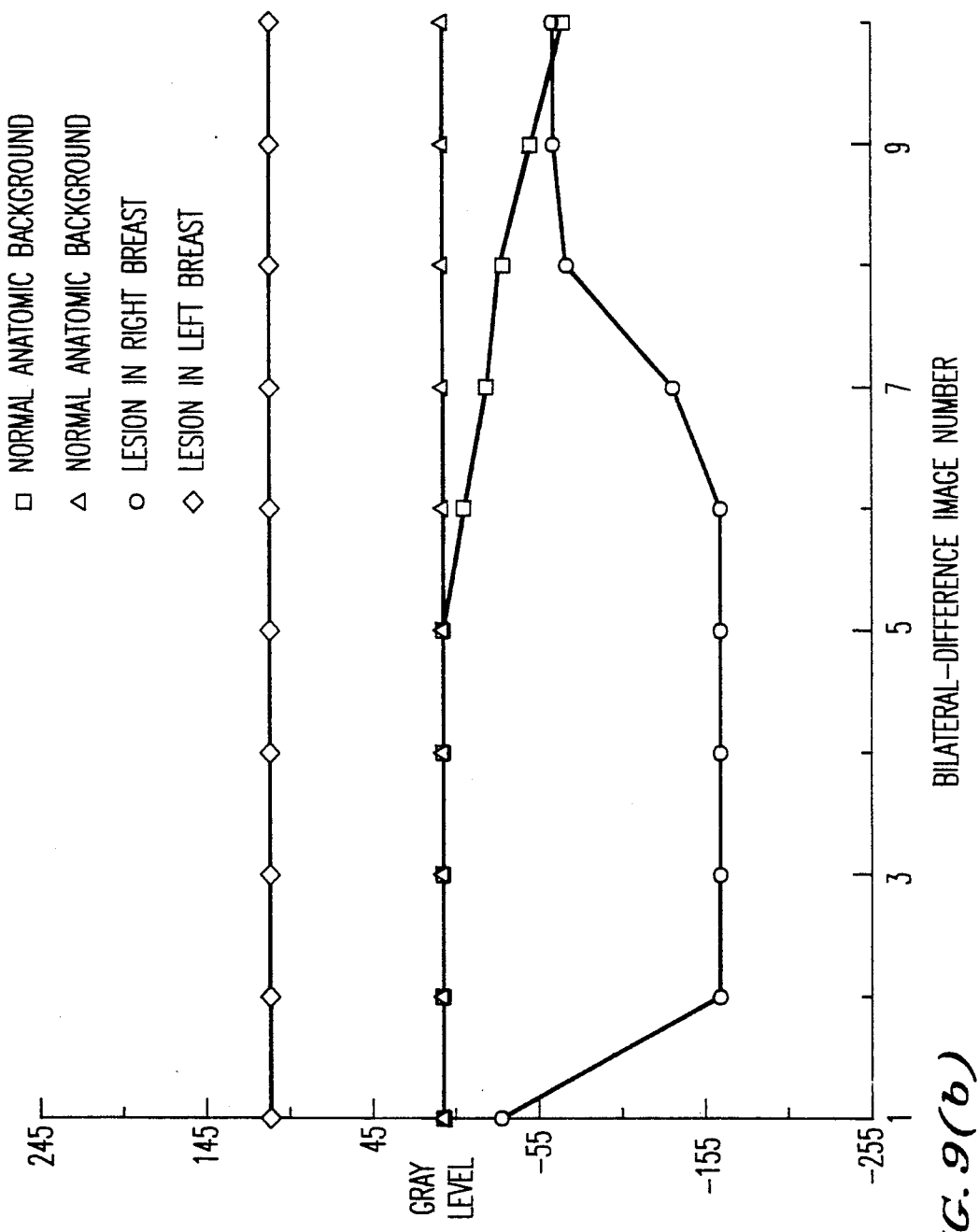
Figure 10A:
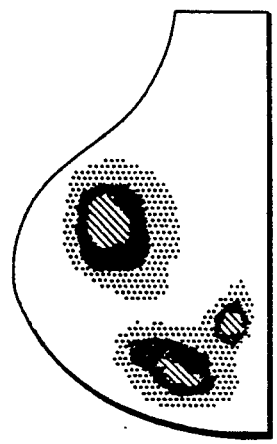
FIGS. 10(a) and 10(b) are illustrations of the two resulting images containing the runlength information from FIG. 8.
Figure 10B:
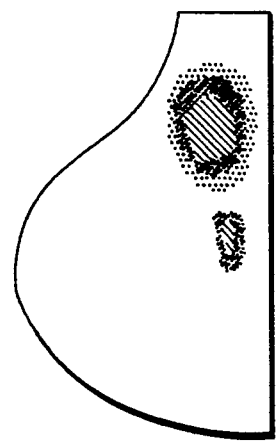

FIGS. 9(a) and 9(b) illustrate the variation of gray level at a specific pixel location as a function of bilateral-difference image for method 3 and method 4, respectively, for a right breast lesion, a left breast lesion and normal anatomic background. Note that with method 3, each pixel location in a bilateral-difference image can be only one of three gray levels (shown here as +1, 0, or −1), whereas with method 4, each pixel location can have a gray level between +255 and −255 (for 8-bit original images). At each pixel location, for a given gray level cutoff, i.e., threshold level, the number of consecutive bilateral-difference images, i.e., the runlength, that contains a gray level equal to or greater than (or equal to or less than for the negative values) the cutoff is used as an indicator of a possible lesion. This runlength information for each pixel of the left and right images derived from the N bilateral difference images is utilized to form left and right runlength images which are stored in memory. When 10 bilateral-difference images are used, the runlength information can be incorporated into two images each with 11 gray levels (including zero): one corresponding to the runlength information for positive values and one corresponding to the runlength information for negative values. FIGS. 10a and 10b illustrate the two resulting images (each having 11 gray levels) containing the runlength information from FIG. 8. Regions of increased intensity in FIGS. 10(a) and 10(b) correspond to locations of suspected lesions and parenchymal distortions in the left and right breasts, respectively. These regions are subjected to feature-extraction (step 490 or 590), as described below.

Figure 11:
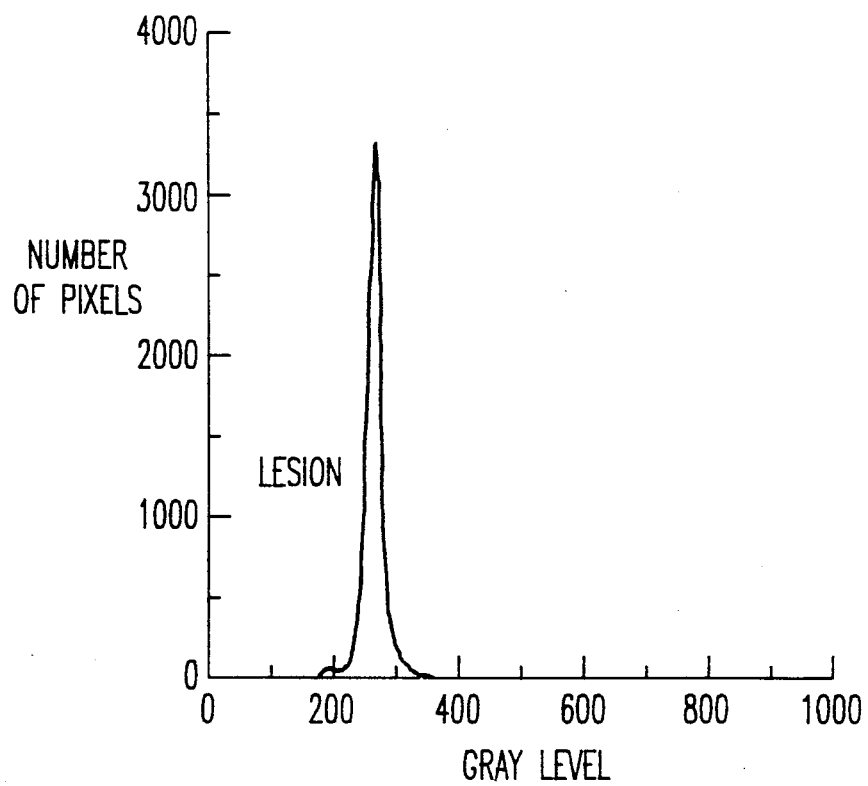
FIG. 11 is a graph illustrating the histogram of a bilateral-difference image obtained with method 2.

With all four methods, thresholding (with respect to gray level for methods 1 and 2, and with respect to runlength for methods 3 and 4) is then performed in order to extract those pixel locations corresponding to possible lesions (step 140). FIG. 11 illustrates the gray-level histogram of a bilateral-difference image obtained by method 2. It should be noted that the image is subjected to thresholding from both ends of the gray-scale in order to detect lesions in both the left and right images. That is, from the upper end, pixel values below the threshold level are set to a constant value, giving rise to an image of "islands", and also, from the lower end, pixel values above an equivalent threshold level (equivalent with respect to equal percentage under the area of the histogram) are set to a constant value giving rise to another image of islands. For example, for the mammograms used for illustration of the histogram in FIG. 11, the lesion existed in the right breast and thus, it would be extracted during the thresholding process from the lower end of the histogram due to the left-minus-right convention. The islands are located automatically with simple computer searching techniques and then submitted to various pattern recognition techniques such as tests for size, relationship to the breast boundary and relationship to mammograms obtained at another view in order to reduce the number of false-positive detections.

Figure 12:
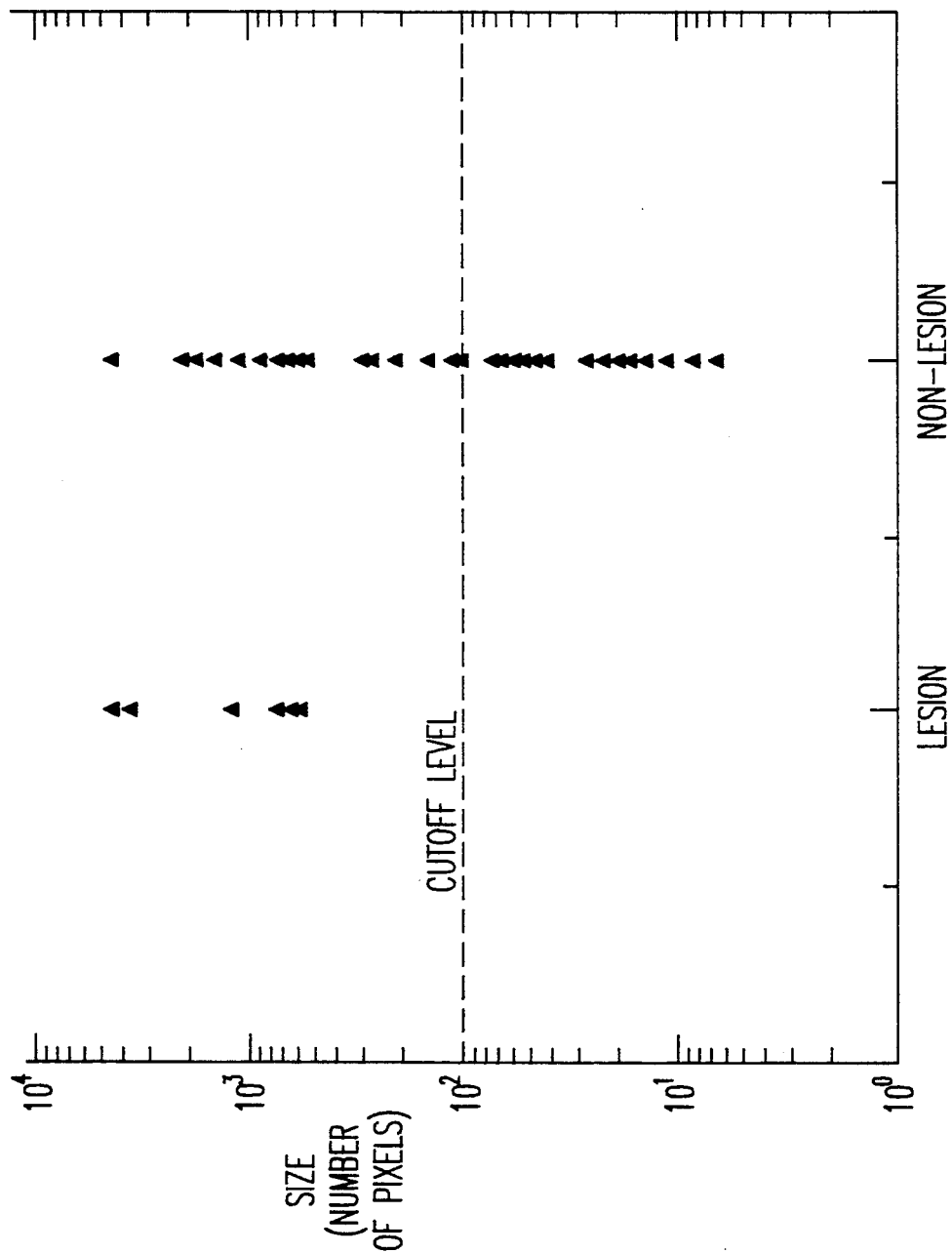
FIG. 12 is a graph illustrating the areas of islands arising from lesions and non-lesions for use in determining the cutoff for the size test.

In the size test (step 150), the number of connected pixels comprising one of the islands is determined, and if the size (i.e., the area in terms of the number of pixels) is too small, the island is eliminated as a possible lesion. FIG. 12 illustrates the distributions of the sizes (in terms of number of pixels) of islands corresponding to lesions and of islands corresponding to non-lesions (i.e., those arising from normal anatomic background). It is apparent that use of a size-cutoff of 100 pixels could substantially reduce the number of false-positive detections (i.e., reduce the number of islands corresponding to normal anatomic background).

Figure 13:
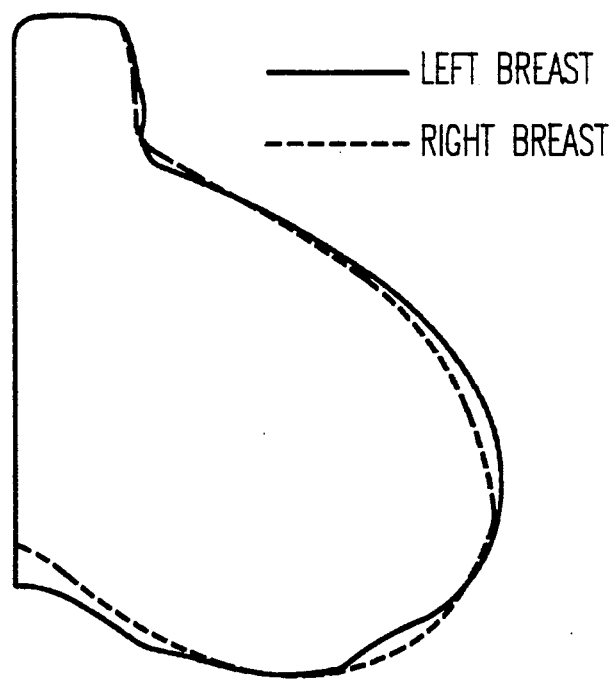
FIG. 13 is an illustration of the tracked boundaries of left and right breast images.

Even though at the start of the detection scheme the boundaries of each breast are determined in the left and right images and aligned spatially to each other, perfect alignment may not result, as illustrated by the breast boundaries in FIG. 13. Thus, in the bilateral difference images an artifact may occur near the boundary and present itself as a possible lesion, as demonstrated in FIGS. 14a and 14b where the indicated islands correspond to possible lesions in the (a) left breast and the (b) right breast, respectively. The islands near the breast boundaries in FIGS. 14a and 14b correspond to a boundary artifact. Therefore, a boundary test (step 160) is used to check the location of the pixels within an island relative to the common boundary of the two images. In the boundary test, the distance of each pixel in the island from the breast boundary is calculated using the square root of the quadratic sum of the distance in the x-direction and the distance in the y-distance. The average distance (in terms of number of pixels) is then determined from distances calculated for each pixel in the island. If this average distance is less than a predetermined distance from the boundary, the island is eliminated as a possible lesion.

In the correlation test (step 170), more false-positive detections are eliminated by correlating the spatial locations of suspected lesions, obtained from mammograms of one view (e.g., cranio-caudal) to those obtained from mammograms of another view (e.g., mediolateral). This test is illustrated schematically in FIG. 15 for a lesion and a non-lesion. For a given island, if a corresponding depth location dx relative to the breast boundary cannot be found in the image of the other view, then the island is eliminated as a possible lesion.

The pixel locations of features, remaining after all the feature-extraction techniques, are then reported as locations of possible breast lesions (step 180). The locations of suspected lesions can be reported in terms of an estimated center (x,y matrix location) of the lesion and/or as all the pixel locations comprising the suspected lesion.

Figure 16:
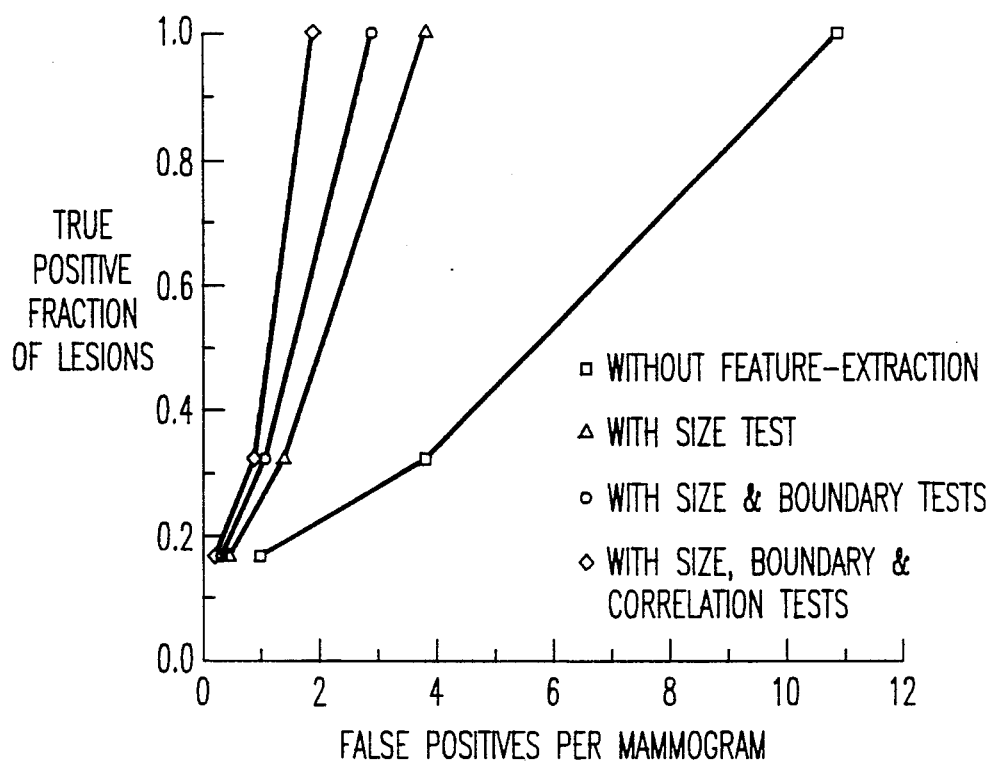
FIG. 16 is a graph comparing the performance of the detection scheme with the use of the various methods for correlation of the multiple-image data.

FIG. 16 illustrates the effect of the various feature-extraction techniques on the performance of the detection scheme using method 4. It is apparent that use of these techniques substantially reduces the number of false-positive detections.

Figure 17:
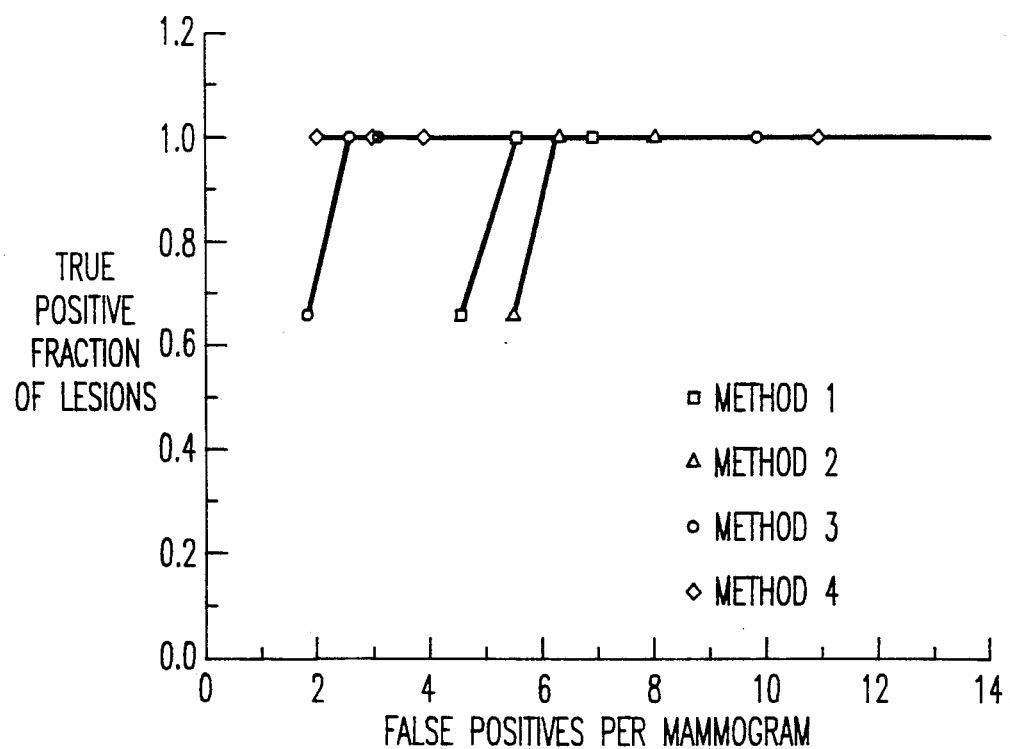
FIG. 17 is a graph comparing the performance of the detection scheme in combination with the various feature-extraction techniques (size test, boundary test, and correlation test).

FIG. 17 illustrates the detection performance of the four methods. The curve for each of the four methods was generated from four points corresponding to the true-positive fraction and the number of false-positive detections per image prior to feature-extraction techniques, after just the size test, after just the size and boundary tests, and after all three feature-extraction tests. Currently, with the disclosed detection schemes, 100% detection of lesions (using 6 pairs of mammograms) has been achieved with a minimum false-positive rate of approximately two false positives per mammogram. Methods 3 and 4 yielded a smaller number of false positives than do methods 1 and 2. However, statistical significance cannot be determined with regard to the differences between any of the four methods due to the limited database, and thus, each of the methods should be considered as feasible for the detection of lesions.

It should be noted that once digital mammograms are input to the computer, the lesion and the distortion detection process is totally automated. After the locations of suspected lesions are found by the computer, the detection results can be presented to a radiologist or serve as an input to the classification part of the overall computer scheme.

Figure 18:
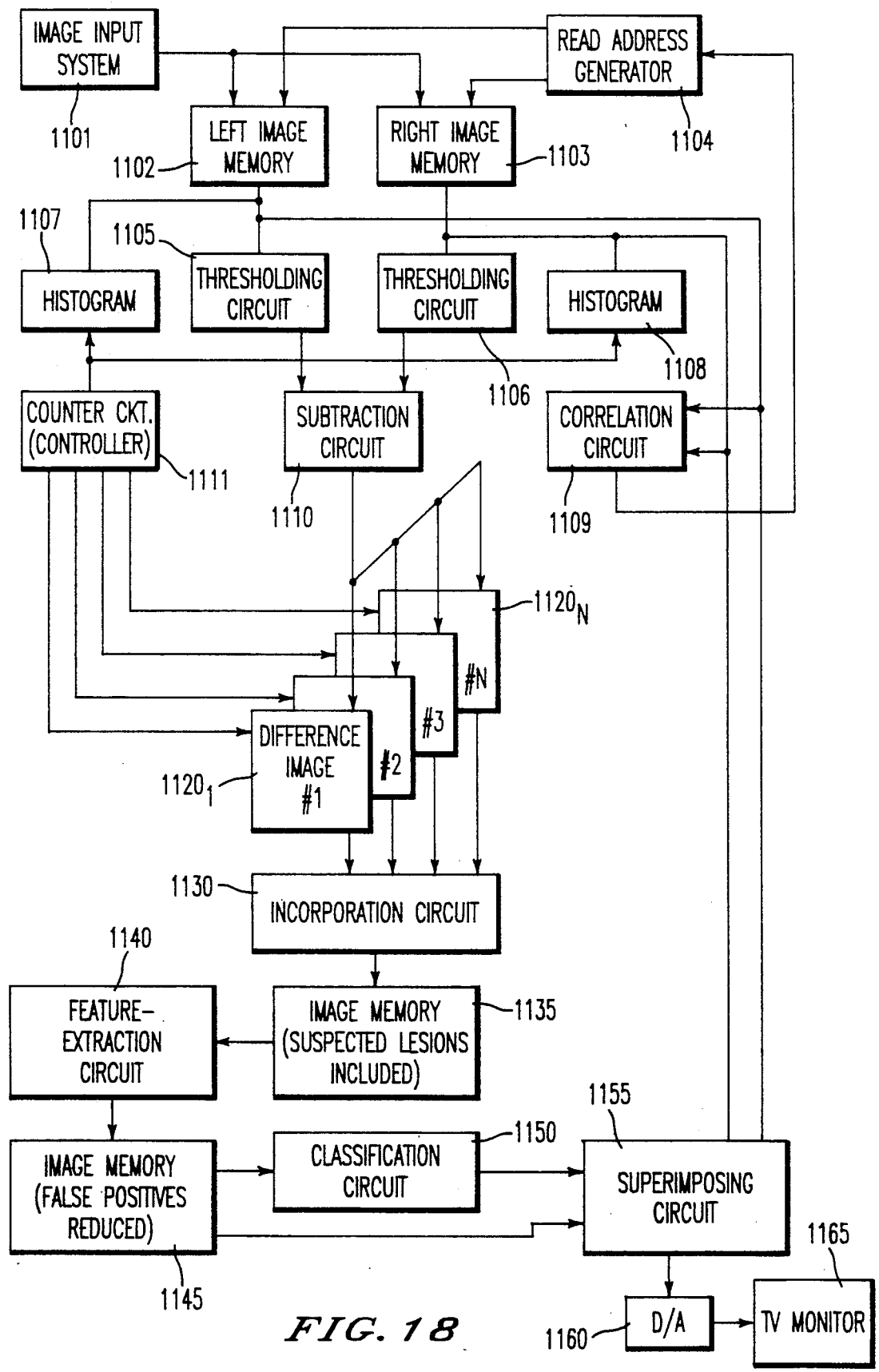
FIG. 18 is a schematic block diagram illustrating a system for implementing the automated method for lesion and parenchymal distortion detection shown in FIG. 2.

FIG. 18 is a more detailed schematic block diagram illustrating a system for implementing the method of the invention. Referring to FIG. 18, x-ray measurements of an object are obtained from an image signal generator and input to the system 1101, for example, the output of the television camera in a fluoroscopic system or a film digitizer for digitizing clinical film images, etc. The left image signals are applied to a first multiple image memory 1102 and the left image signal are applied to another multiple image memory 1103. The signals in those memories can then be shifted by the read address generator 1104 in order to maximize the alignment of the images in question. Translation, rotation and if necessary warping of the boundaries from the multiple images is performed in order to obtain maximum correlation (1109) and align the images.

Correlation of the image data is shown in FIG. 18 for method 4. Data in each of the memories (1102 and 1103) are subjected to a threshold circuit 1105 and 1106, each of which utilizes a device for determining the gray-level histogram (1107 and 1108). There the correspondence between gray-level cutoff and area under the respective histogram is determined. The corresponding gray-level threshold images for the left and right breast images are then subjected to the subtraction circuit 1110. A counter circuit (controller) 1111 is used to keep track of the number of threshold levels requested. This number also determines the number of difference images calculated by the subtraction circuit 1110 and stored in the corresponding memory locations ($1120_1$, $1120_2$, ..., $1120_N$) The incorporation circuit 1130 determines the runlength information for each pixel location in the image matrix which is stored in image memory 1135. The resulting images provide increased conspicuity of the suspected abnormalities. The suspected features in the image memory 1135 are then subjected to the feature-extraction circuit 1140. In the feature-extraction circuit 1140, measures for the size of the feature (island), relationship to the boundary of the body part and relationship to features located in images obtained from other projection views are determined. Determination is made whether the given feature is an actual lesion or a non-lesion (arising from normal anatomic background) by comparing with predetermined values. These results are stored in image memory 1145. The results can be input to the classification device 1150 for determination of possible malignancy of the suspected lesion or parenchymal distortion.

The results from the image memory 1145, with or without the output from the classification device 1150, are applied via a superimposing circuit 1155 on the original images, and displayed on the display system 1165 after passing through a digital to analog convertor 1160.

Figure 19:
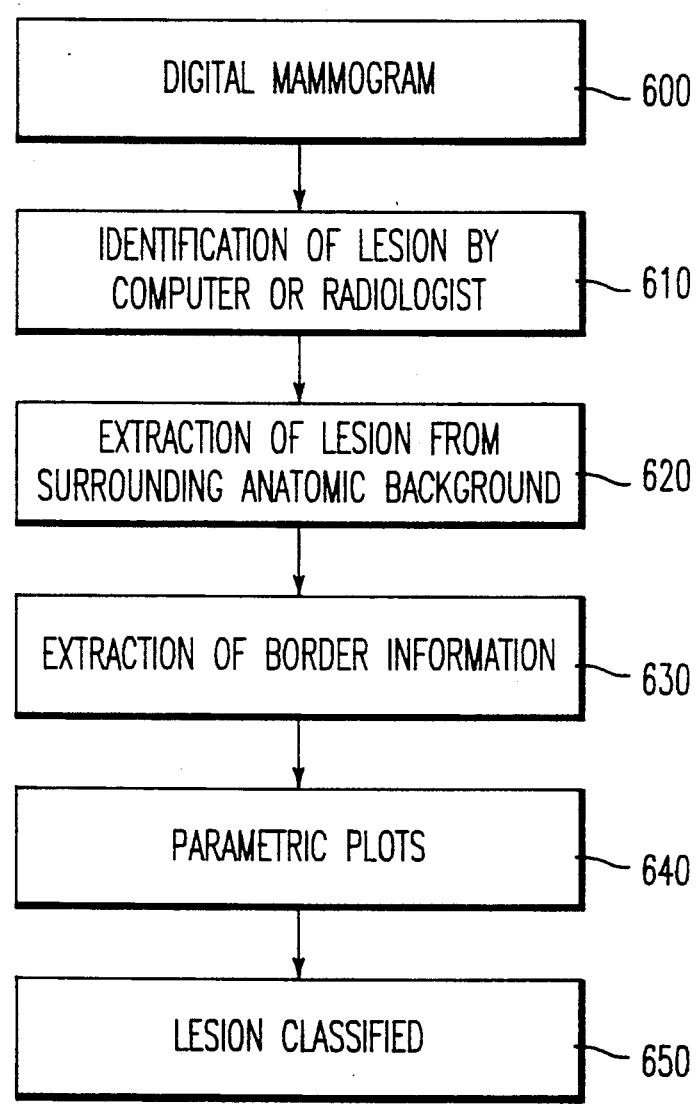
FIG. 19 is a detailed schematic diagram illustrating an automated method for lesion and parenchymal distortion classification alone according to the invention.

In the classification process shown in FIG. 19, a novel technique is used in an attempt to isolate the fluctuations (i.e., spiculations) about the border of the lesion in the mammogram (600) for subsequent analysis. The input to the classification part of the automated scheme can be either the pixel locations of possible lesions found in the detection part or pixel locations indicated by a radiologist (e.g., by a trackball) (step 610). The input of the pixel locations could be in a fashion such as the estimated center of the lesion and/or the estimated border of the lesion as derived either from the automated detection part or as indicated by a radiologist.

It should be noted that the digital data of the breast images for the classification process require sufficient spatial resolution in order to quantify the high-frequency spiculations of the lesion (to be described later). For the results presented here, a optical drum scanner (film digitizer) with a sampling pixel of 0.1 mm was used in the digitization of clinical screen/film mammograms. Note that such high spatial resolution is not required in the detection process (described earlier) due to the relatively large size of lesions. The results of the detection process were obtained using a TV film digitizer with a 512 by 512 matrix, which yielded a pixel size of approximately 0.4 mm.

It should be noted that a key component in the classification scheme is the extraction and analysis of the border information of the lesion in question (step 630). However, prior to this extraction of border information, the lesion must be distinguished from the surrounding anatomic background (step 620). Various methods can be used in order to initially separate the lesion from the anatomic background. Region growing (to be described later) can be used to extract the lesion from the surrounding parenchymal patterns. Another method involves inputting to the computer a radiologist hand-drawn depiction of the lesion and its border. Yet another method involves using edge-detector digital filters (such as a gradient or Laplacian) (See Pratt, Digital Image Processing, Wiley (New York, 1978)) applied on the original image in order to highlight the fall-off of pixel values at the border of the lesion in question. Also, when the classification scheme is used together with the detection process (previously described), the resulting detected feature can be used as an indicator of the lesion.

Figure 20:
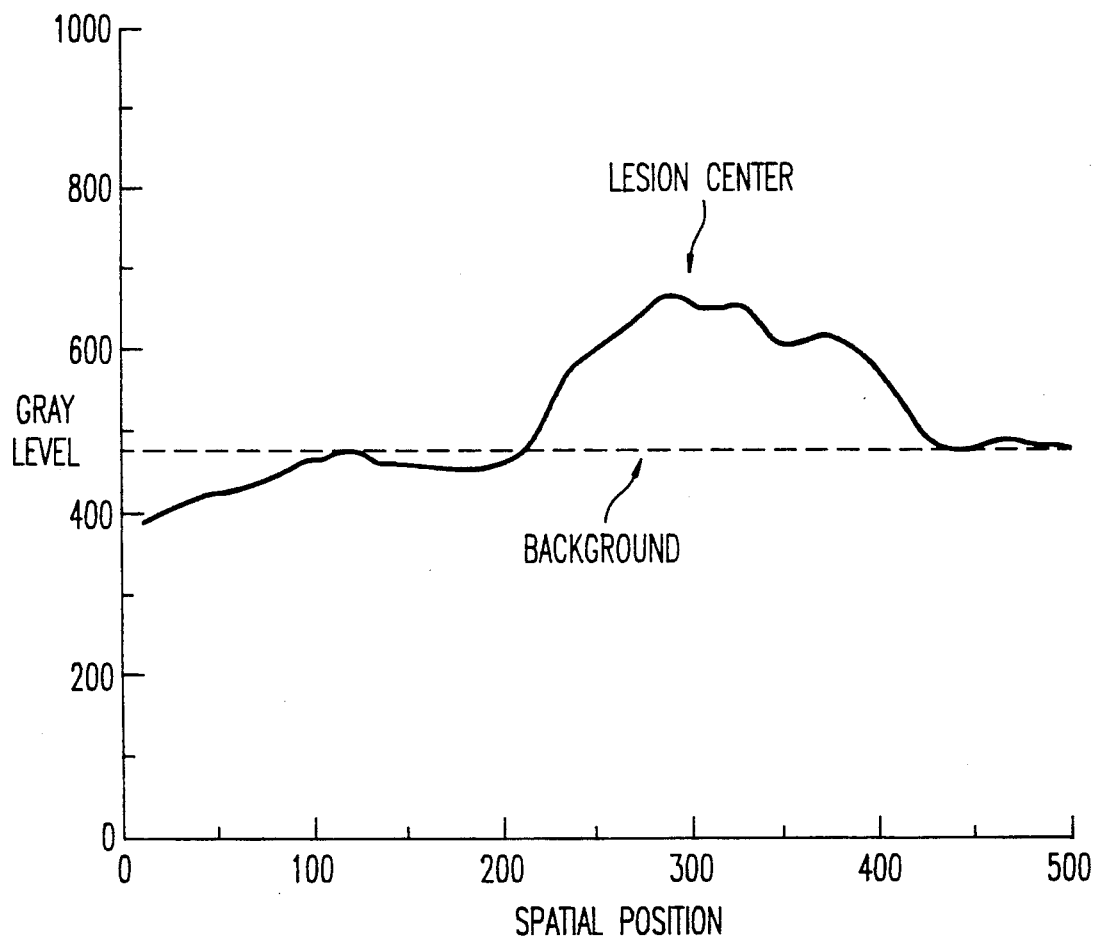
FIG. 20 is a graph illustrating the profile across mammographic lesion.

One method for extracting the lesion in question from the surrounding parenchymal patterns (step 620) is to perform region-growing from the approximate center of the lesion. (If only the pixel locations of an estimated border of the lesion were input to the classification scheme, an approximate center could be obtained by calculating the centroid from the pixel location of the border.) In order to determine the gray-level interval suitable for region growing, horizontal and vertical profiles across the image of the lesion are calculated. From these profiles, of which an example of a horizontal profile is illustrated in FIG. 20 for a mammographic lesion, the difference between the gray levels of the center (of the lesion) and the background is used to yield the interval for region growing. A simple approach to determine the gray level of the background is by calculating the maximum of four values: the 0 and 511 pixel locations in the horizontal profile and the 0 and 511 pixel locations in the vertical profile. Other methods to determine the background are possible, such as using a polynomial fit to the overall global trend of the mammogram (See Bevington, Data Reduction and Error Analysis for the Physical Sciences (McGraw-Hill, 1969)). Region-growing techniques (See Pratt, supra) are employed in order to obtain a binary ("silhouette") image of the lesion (i.e., the "grown" lesion), as illustrated later in FIGS. 23 (a) and 23 (b) which demonstrate the outlines of typical grown regions. Region growing employs 8-point connectivity in order to determine which pixel locations have gray levels within the specific interval and are also connected to the center (of the lesion) pixel location. Multiple gray-level intervals (corresponding to multiple background values) can be employed to obtain a series of grown images, from each of which border information can be extracted for analysis.

Extraction of the border information (step 630) from the grown lesion can be performed by various methods as illustrated in FIG. 21. All the methods involve some type of smoothing step, after which a comparison is performed between the smooth data and the original data. The purpose of the smoothing step is to eliminate the border fluctuations corresponding to the spiculations of the lesion. The comparison is formulated into some quantitative difference. Since malignant lesions usually exhibit a high degree of spiculation, a large difference between the original data and the smooth data would indicate a high degree of malignancy. Results obtained from more than one of the methods can be combined to increase the accuracy and reliability of the classification scheme.

Figure 21A:
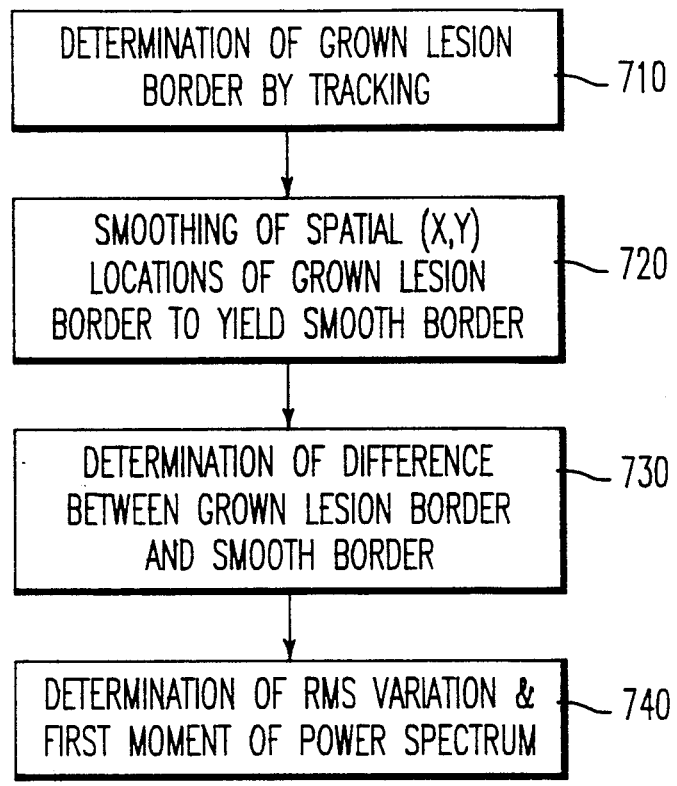
FIGS. 21(a), 21(b), 21(c) and 21(d) are schematic diagrams illustrating methods A, B, C, and D, respectively, for the extraction of the border information of the lesion in question.
Figure 22A:
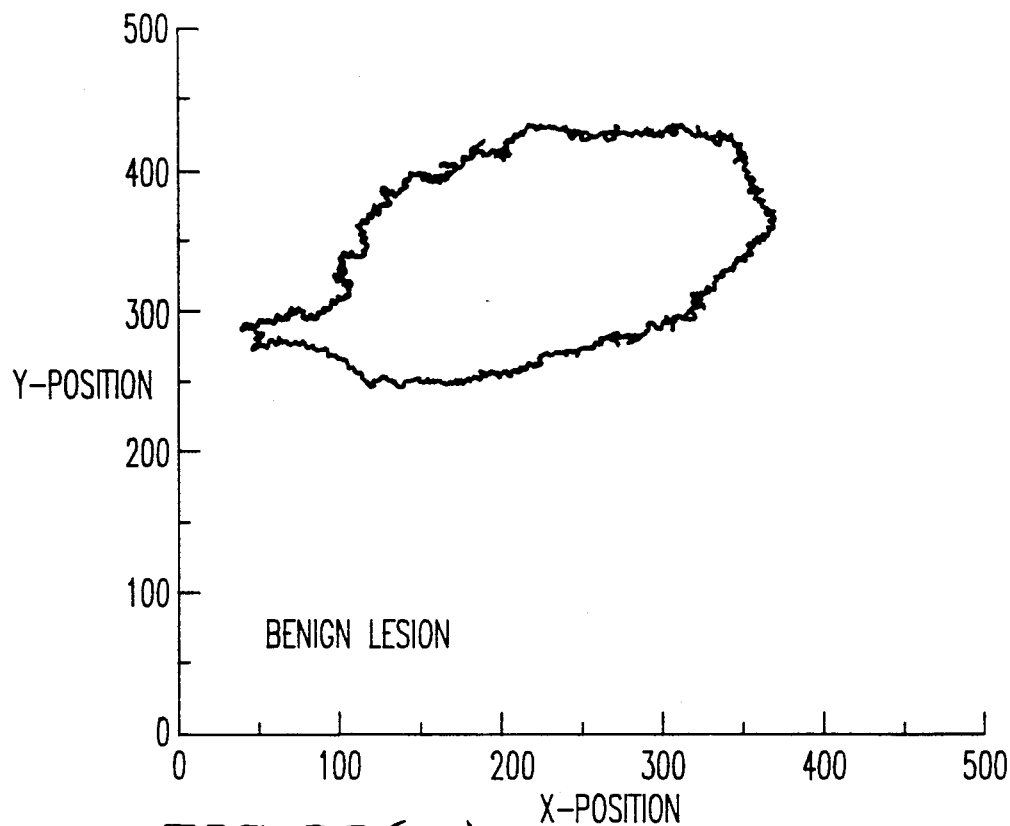
FIGS. 22(a) and 22(b) are illustrations demonstrating the tracked border of (a) a benign lesion and (b) a malignant lesion, respectively.
Figure 22B:
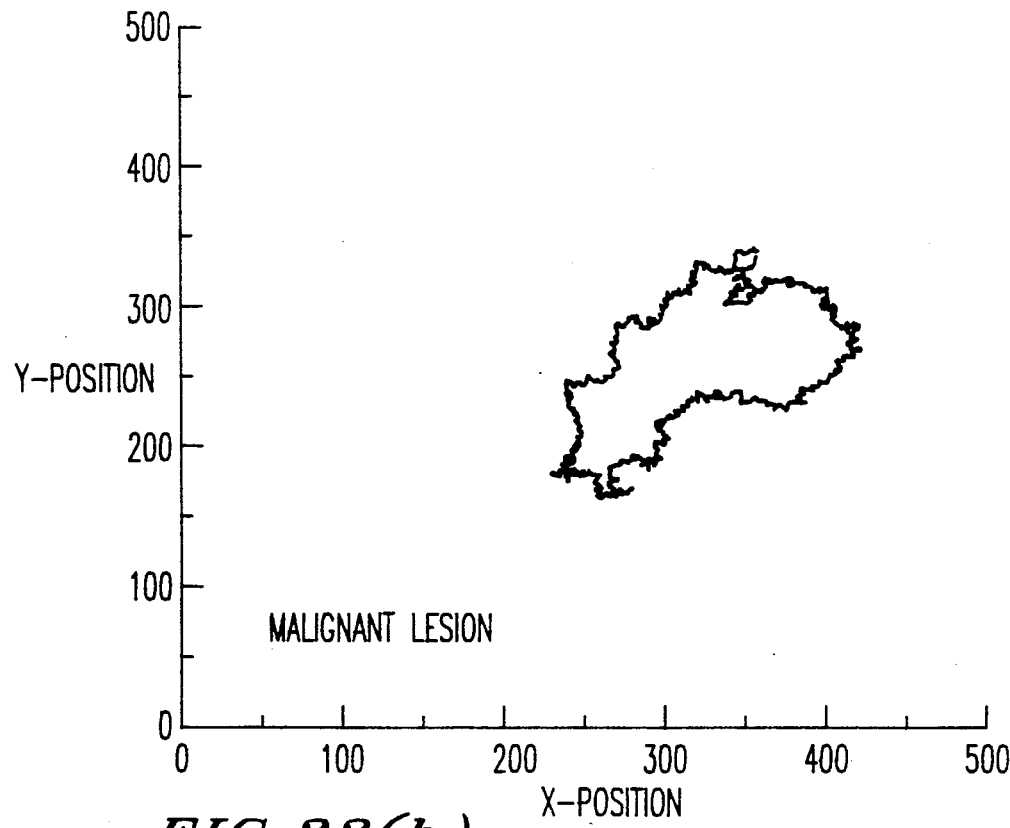
Figure 23A:
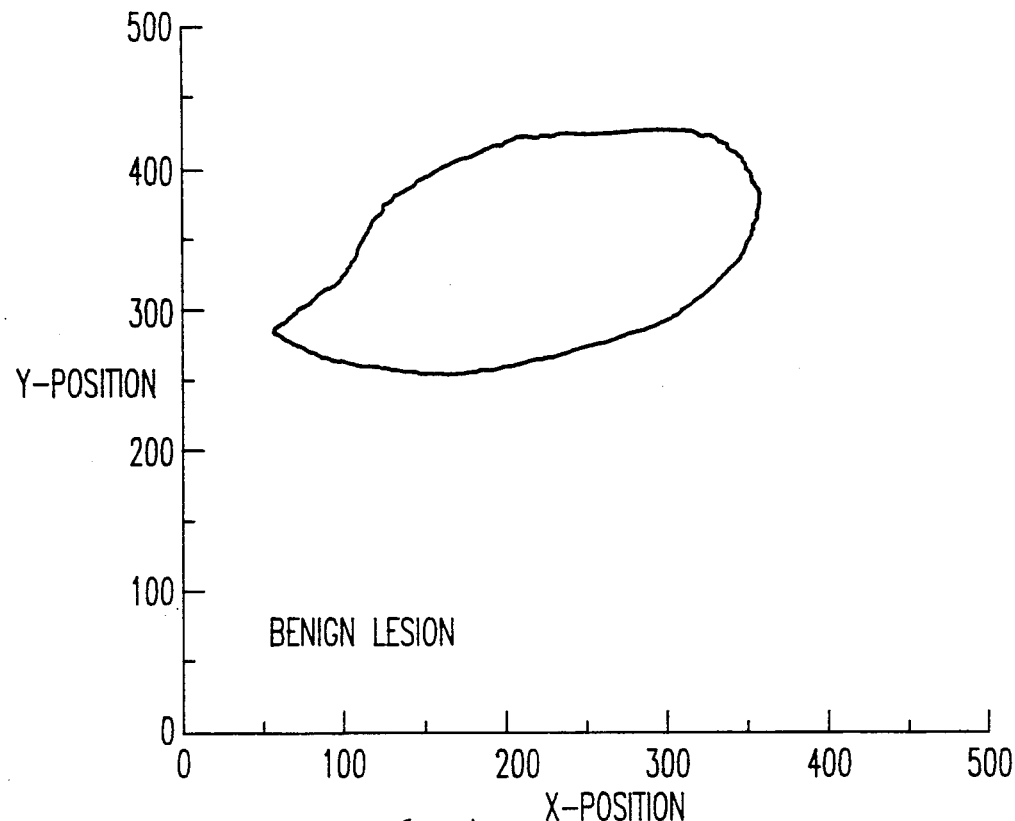
FIGS. 23(a) and 23(b) are illustrations demonstrating the smooth border of (a) a benign lesion and (b) a malignant lesion, respectively.
Figure 23B:
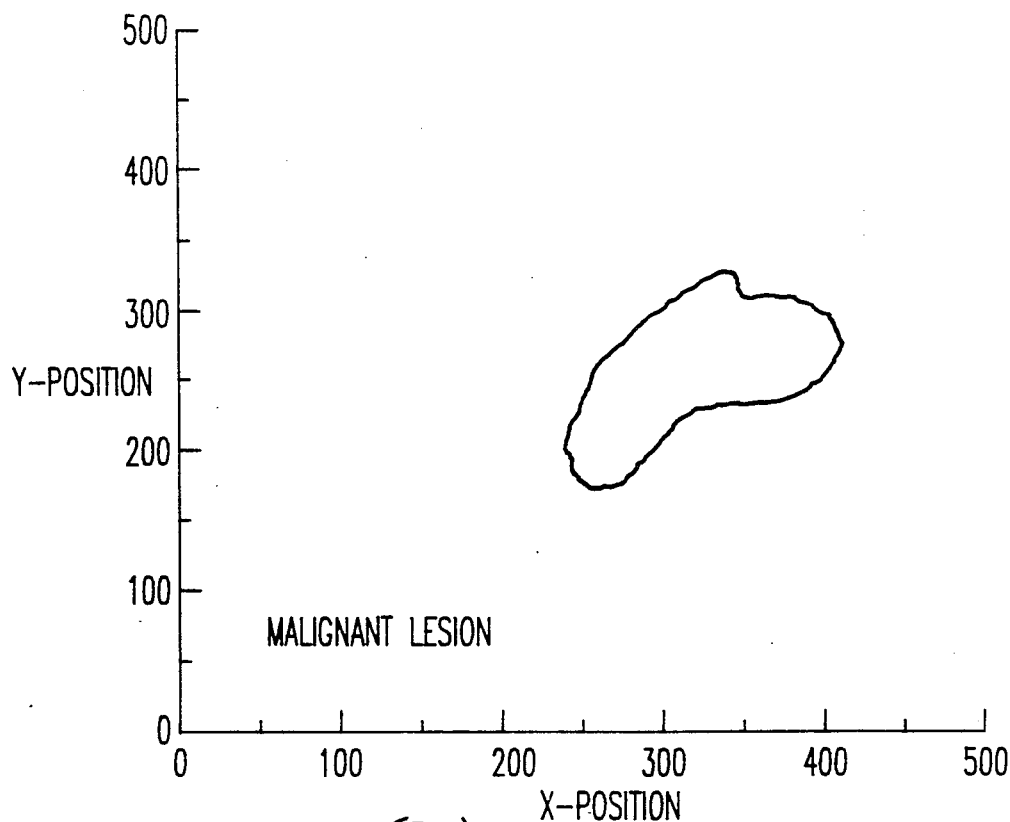

In method A (as indicated in FIG. 21(a)), the border of the binary image (i.e., grown lesion) is determined using simple computer border-tracking methods such as those employing 4-point or 8-point connectivity (See Pratt, supra) (step 710). This border is saved in terms of cartesian or polar coordinates. FIGS. 22(a) and 22(b) illustrate the tracked border of a grown lesion for (a) a benign lesion and (b) a malignant lesion, respectively. A smooth border of the lesion is determined from smoothing the spatial locations of the tracked border of the grown lesion (step 720). FIGS. 23(a) and 23(b) illustrate the smooth border for (a) the benign lesion and (b) the malignant lesion, respectively. The smooth borders were obtained by a running mean filtering of the spatial locations of the tracked borders of the grown lesions. The size of the running mean was equal to approximately 10% of the border length (i.e., the number of pixels in the border.) It is apparent that the spiculations evident in the malignant lesion have been reduced in the smooth borders. The difference in the borders (i.e., the original border of the grown lesion and the "smooth" border) are calculated (step 730). This difference was obtained from the square root of the quadratic sum of the difference in the x-positions and the difference in the y-positions for corresponding points in the original and smooth borders. (Other methods, such as determining the perpendicular distance between the borders, can also be used in determining the difference between the borders.) This difference yields the fluctuations about the border of the lesion corresponding to the spiculations.

Figure 24A:
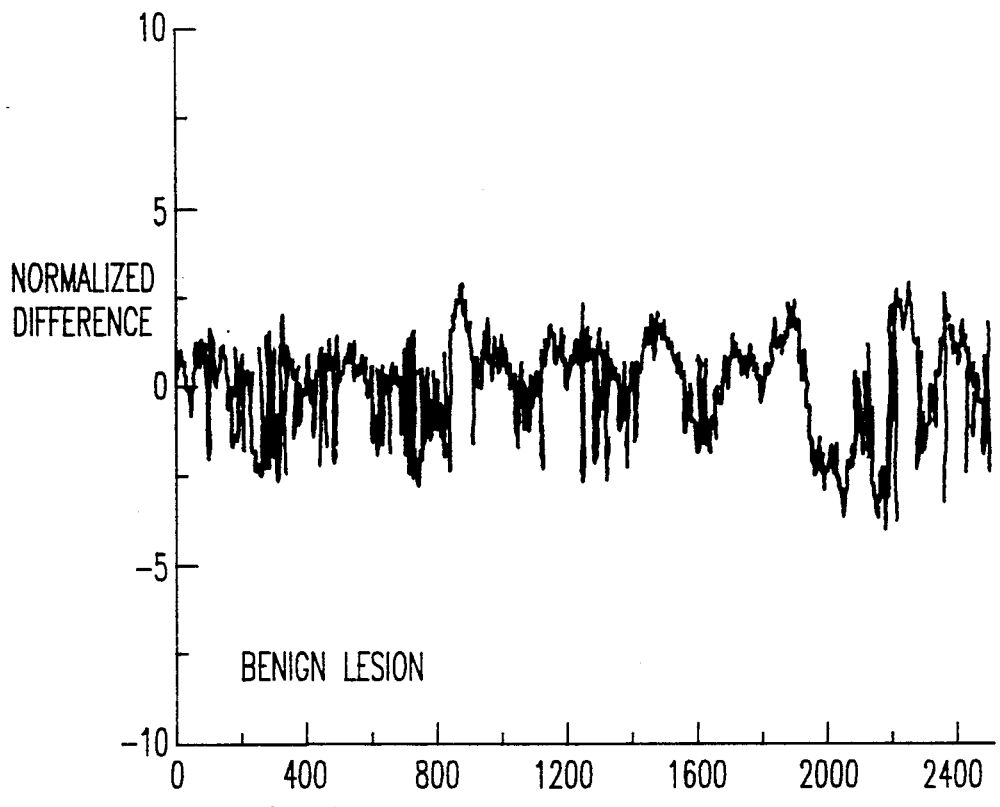
FIGS. 24(a) and 24(b) are illustrations demonstrating the difference between the lesion border and the smooth border for (a) a benign lesion and (b) a malignant lesion, respectively.
Figure 24B:
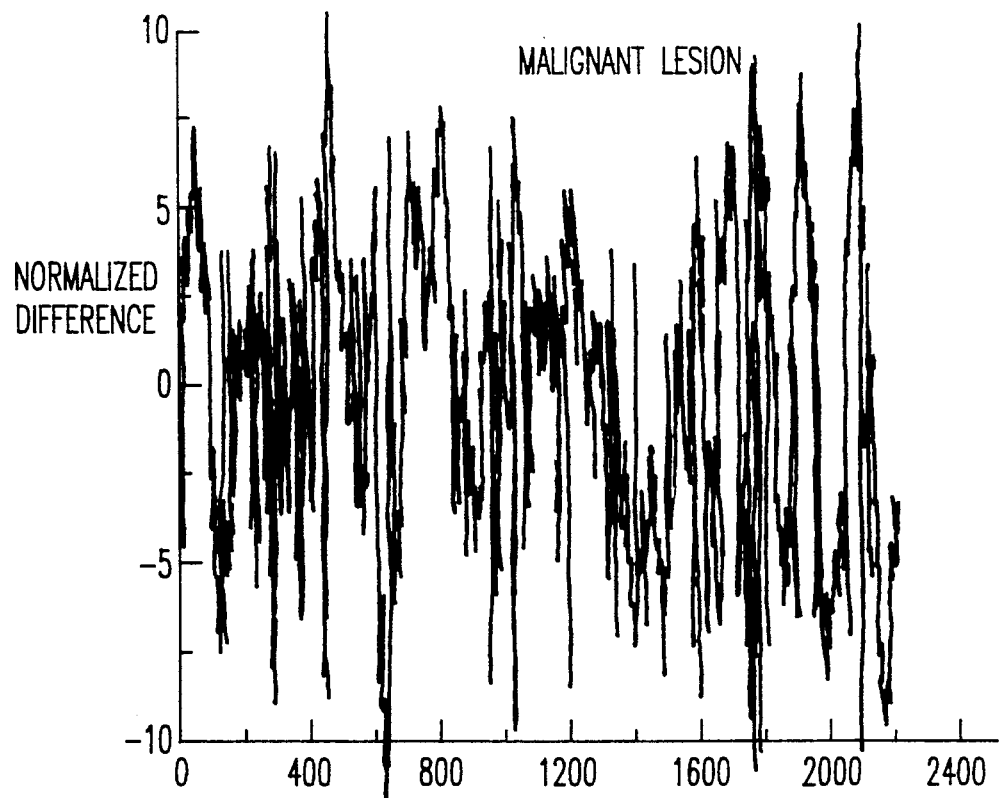
Figure 25:
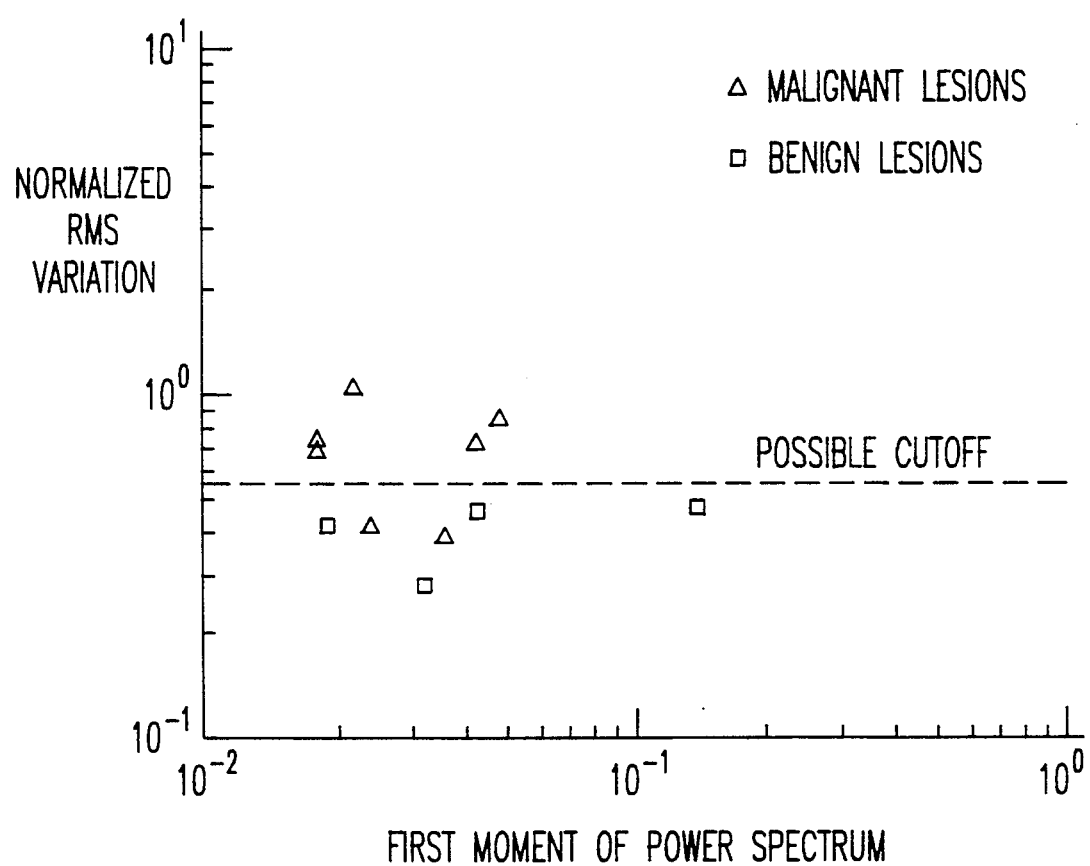
FIG. 25 is a graph illustrating the calculated parameters (normalized rms variation and first moment) of the border fluctuations for benign and malignant breast lesions.

FIGS. 24(a) and 24(b) illustrate the border fluctuations for (a) the benign lesion and (b) the malignant lesion respectively. The discrete Fourier transform (See Bracewell, The Fourier Transform and Its Application, McGraw-Hill (New York, 1978)) of the spiculations (i.e., the fluctuations) is calculated, and the rms variation and the first moment of the power spectrum (See Bracewell, supra) is determined (step 740). Border fluctuations with large rms variations correspond to highly spiculated lesions, the majority of which are malignant. FIG. 25 illustrates the rms variation and the first moment for various benign and malignant lesions. For this example, the smooth border was obtained by using a running-mean filter (See Pratt, supra) on the spatial locations of the tracked border of the grown lesion.

Figure 21B:
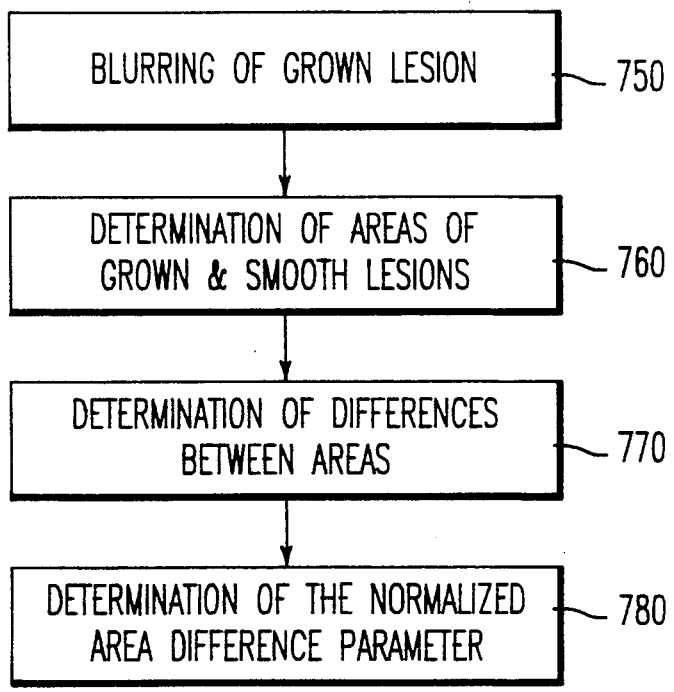
Figure 26:
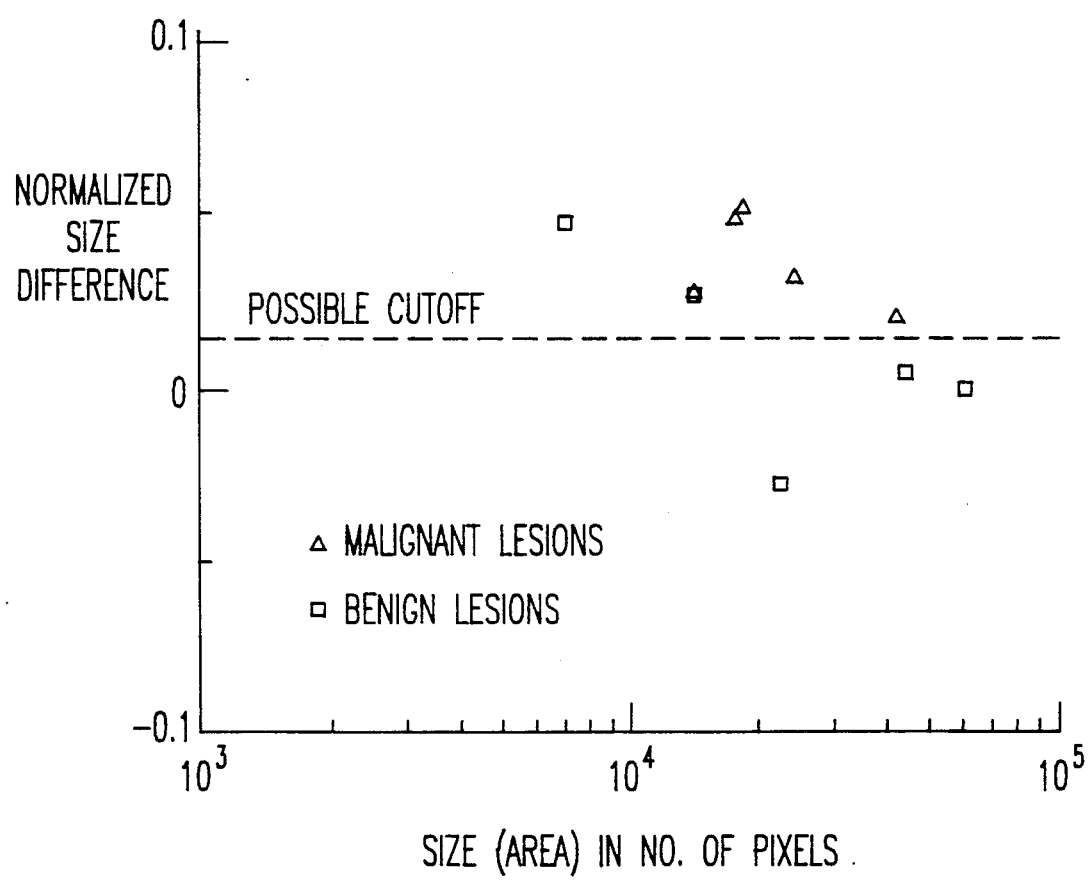
FIG. 26 is a graph illustrating the clusters of calculated parameters (normalized difference in area) for benign and malignant breast lesions.

In method B of FIG. 21(b), the grown lesion is subjected to a blurring process (step 750). The areas of the grown lesion and the blurred lesion are determined in terms of number of pixels (step 760). The difference between the areas of the two lesions is calculated (step 770) and then normalized to the area of the grown region (step 780). Since blurring of the grown lesion results in a reduction of any spiculations in the border, the area is expected to be less for the smooth lesion than for the grown lesion. Thus, a large difference in the areas between the grown lesion and the blurred lesion serves as an indicator of malignancy, since malignant lesions tend to have border spiculations which tend to be lost during the blurring process producing a larger difference. FIG. 26 illustrate the normalized size differences for benign and malignant lesions. For this example, the blurred lesion was obtained by using a morphological filtering (See Serra, Image Analysis and Mathematical Morphology, Academic Press (New York, 1982)) sequence of dilation (circular kernel of radius 2 pixels), errosion (circular kernel of radius 8 pixels) and dilation (circular kernel of radius 6 pixels).

Figure 21C:
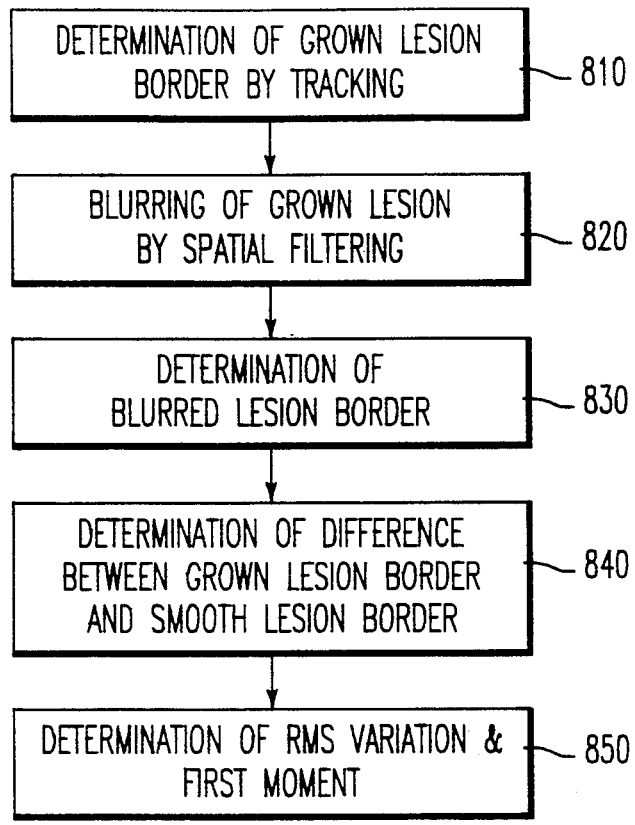

In method C of FIG. 21(c), the border of the grown lesion is determined using simple computer border-tracking methods (step 810). Next, the grown lesion is blurred using spatial filters such as averaging filters (See Pratt, supra) or morphological filters (See Serra, supra) (step 820). The border of the smooth lesion is then determined using similar border-tracking techniques referred to earlier (step 830). The differences in the borders are then calculated (step 840) to yield the fluctuations about the border corresponding to the spiculations. The discrete Fourier transform of these fluctuations is calculated, from which the rms variation and first moment of the power spectrum are determined (step 850).

Figure 21D:
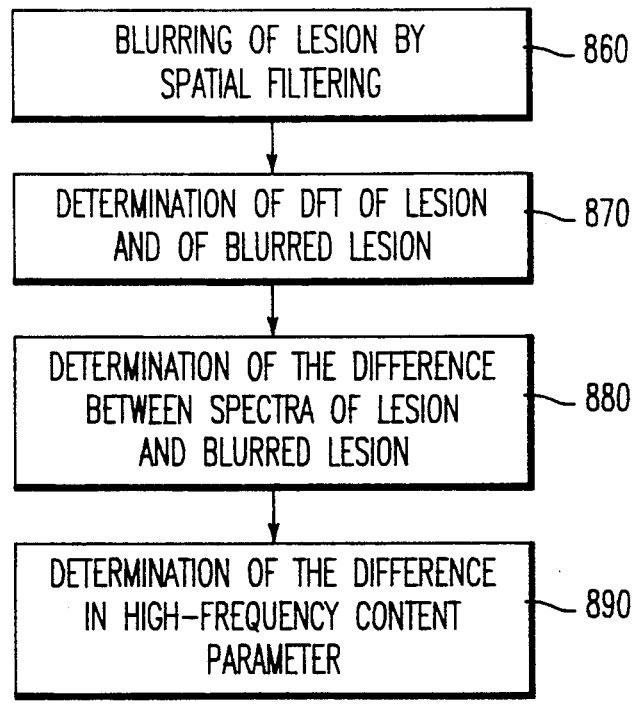

In method D of FIG. 21(d), the lesion is subjected to a blurring process (step 860). The blurring process will reduce the high-frequency content of the spiculated lesion. The two-dimensional discrete Fourier transform (See Bracewell, supra) is determined of the original lesion and of the blurred lesion (step 870). The difference between the spectrum of the lesion and that of the blurred lesion is then determined (step 880). This "difference spectrum" is then subjected to such parametric calculations (step 890) as the rms variation and the first moment in order to quantify the high-frequency differences.

Using parametric plots (step 640 in FIG. 19) (such as those in FIG. 25 for method A and FIG. 26 for method B) as cluster diagrams, cutoffs for malignancy can be determined. For example, lesions having a positive value for the normalized size difference (see FIG. 26) could be considered to be malignant. Each lesion is then classified depending on its relationship to the predetermined cutoff value (step 650). Such a cutoff could be changed in order to vary the sensitivity and specificity of the scheme. For example, for patients at high risk for breast cancer, the cutoff could be varied to increase the sensitivity for correct classification of malignant lesions with the tradeoff of an increased number of benign lesions being classified as malignant. In another situation, such as in a mass screening program stricter criteria for malignancy could be employed in order to keep the number of unnecessary biopsies to a minimum.

Figure 27:
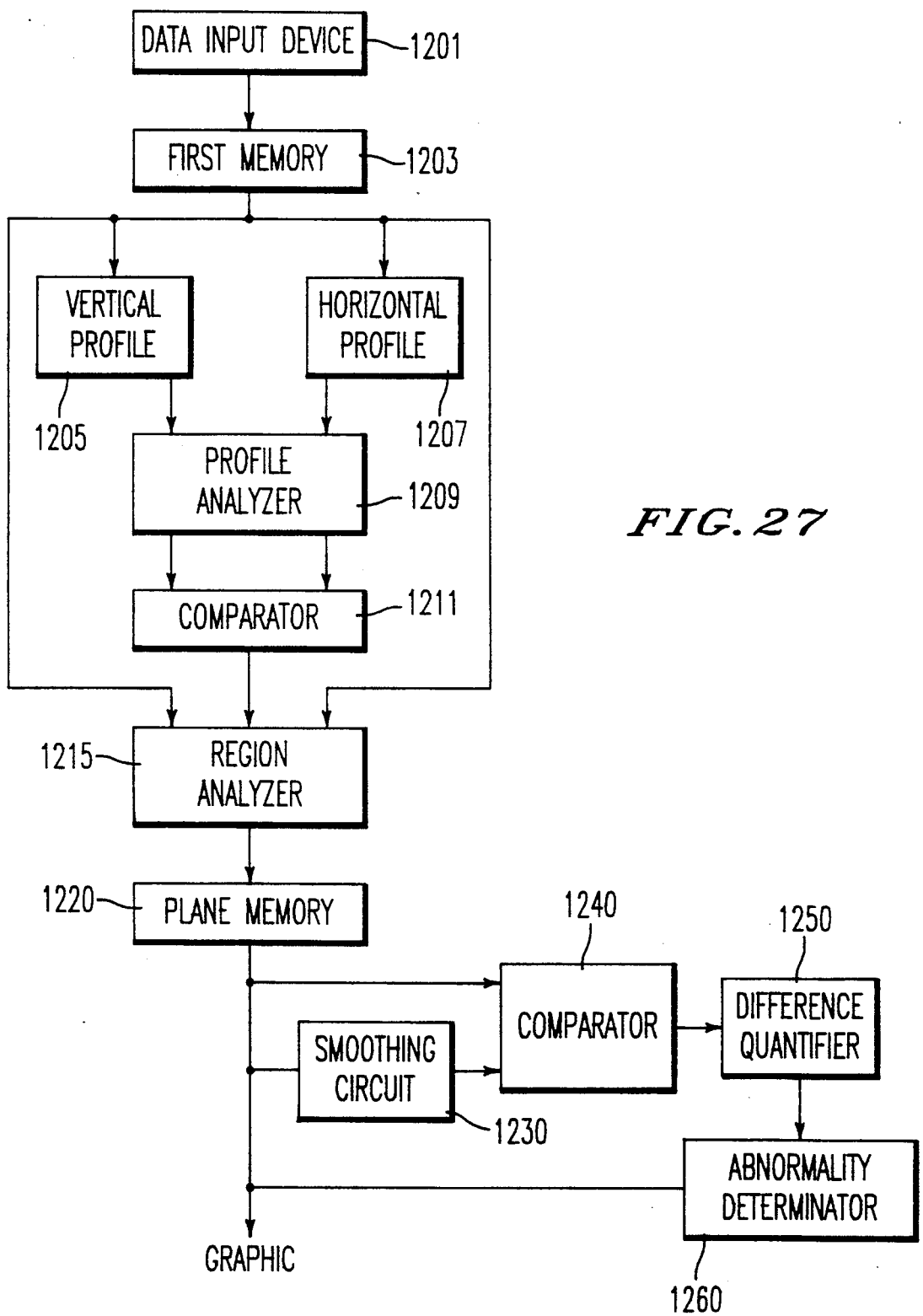
FIG. 27 is a schematic block diagram illustrating a system for implementing the automated classification method shown in FIG. 19.

FIG. 27 is a more detailed schematic block diagram illustrating a system for implementing the classification portion of the method. This system can be considered as a sub-system of the detection system or as a system on its own. Referring to FIG. 27, pixel locations of suspicious lesions or distortions are accepted by the classification system from either a radiologist or the automated detection scheme by means of the data input device 1201. The image signals from the image input device 305 and the input data are applied to a first memory 1203.

Lesion extraction is performed using a profile method to determine the number of gray levels spanned by the lesion of interest. Data from the memory 1203 is input to devices 1205 and 207 for determining the vertical and horizontal profiles, respectively. The profile analyzer 1209 determines the gray level of the lesion center and the gray level of the background. The gray-level interval is used to extract the spatial locations of the lesions from the surrounding background and obtain a binary image of the lesion. Multiple gray-level intervals are used to obtain a series of binary images for submission to analyses. Comparator 1211 determines the optimal background level and thus, the optimal gray-level interval for region growing. Region growing is performed on the image data by region analyzer 1215. The region-grown image is then stored in plane memory 1220.

Smoothing circuit 1230 performs the necessary smoothing operations in order to extract the border information from the lesion in question. For example, the smoothing circuit 1230 would smooth the border pixel locations as in the method A of FIG. 21(a). Comparator 1240 calculates the differences between the original data and the smooth data. For example, with method A of FIG. 21(a), the comparator would determine the difference between the original border pixels and the smooth border pixels. Parameters quantifying the differences obtained by comparator 1240 are then calculated by the difference quantifier 1250. Examples of such would be the rms variation and the first moment of the power spectrum (method A) and the normalized area difference parameter (method B).

The difference parameters are then input to abnormality determinator 1260 where determination is made whether the given lesion is either malignant or benign by comparing predetermined values.

The results from the various comparison tests are applied to display system via a superimposing circuit. These results can be displayed alone or in combination with those of the detection device.

Obviously, numerous modifications and variations of the present invention are possible in light of the above teachings. It is therefore to be understood that within the scope of the appended claims, the invention may be practiced otherwise than as specifically described herein.

What is claimed as new and desire to be secured by Letters Patent of the United States is:

1. A method for automated analysis of abnormalities in the form of lesions and parenchymal distortions using digital images, comprising:

generating at least first and second image data from respective of at least first and second digital images derived from at least one selected portion of an object; and correlating said at least first and second image data to produce correlated data in which normal anatomical structured background is removed.

2. The method according to claim 1, further comprising:

searching said correlated data using at least one predetermined criterion to identify in at least one of said digital images an abnormal region represented by a portion of said correlated data which meets said predetermined criterion; and indicating the location of said abnormal region in said at least one of said digital images.

3. The method according to claim 2, wherein said generating step comprises:

determining at least first and second histograms of respective of said at least first and second digital images, determining at least first and second cumulative histograms of said at least first and second histograms, respectively, and matching at least the second cumulative histogram to the first cumulative histogram by modifying data values of pixels of at least the second digital image based on a predetermined relationship between the data of the at least first and second cumulative histograms, said second image data corresponding to modified pixel values of said second digital image and said first image data corresponding to pixel values of the first digital image.

4. The method according to claim 3, wherein said generating step comprises:

determining N at least first and second threshold values, and determining N at least first and second threshold images for each of said at least first and second digital images by comparing each pixel of said at least first and second digital images with each of respective of said N at least first and second threshold values and assigning each said pixel a first predetermined value when said pixel is above the threshold value and a second predetermined value when said pixel is below the threshold value, said first image data being N image data corresponding to the N first threshold images and said second image data being N image data corresponding to the N second threshold images.

5. The method according to claim 4, wherein said step of determining said N at least first and second threshold images comprises:

assigning to each said pixel of said at least first and second digital images a predetermined first constant value or a predetermined second constant value when that pixel has a value above or below said threshold value, respectively.

6. The method according to claim 4, wherein said step of determining said N at least first and second threshold images comprises:

assigning each said pixel of said at least first and second digital images the value of that pixel in the respective digital image when that pixel has a value above said threshold value, and assigning each said pixel of said at least first and second digital images a predetermined constant value when that pixel has a value below said threshold value.

7. The method according to claim 4, wherein said step of determining said N at least first and second threshold values comprises:

determining at least first and second histograms of said at least first and second digital images, respectively, and defining said N at least first and second threshold values as being the pixel values at selected percentages of said at least first and second histograms, respectively.

8. The method according to claim 1, wherein said correlating step comprises:

forming a difference image based on the difference between said first and second image data.

9. The method according to claim 3, wherein said correlating step comprises:

forming a difference image based on the difference between said first and second image data.

10. The method according to claim 4, wherein said correlating step comprises:

forming N difference images based on the difference between the N first threshold images and respective of the N second threshold images.

11. The method according to claim 10, wherein said correlating step further comprises:

forming a first runlength image in which each pixel of the first runlength image corresponds to an identical pixel location in said N difference images and is assigned a value in dependence on the largest number of said identical pixels which in consecutive order of said N difference images have a predetermined positive value, and forming a second runlength image in which each pixel of the second runlength image corresponds to an identical pixel location in said N images and is assigned a value in dependence on the largest number of said identical pixels which in consecutive order of said N difference images have a predetermined negative value.

12. The method according to claim 9, wherein said searching step comprises:

comparing the value of each pixel of said difference image with a predetermined threshold value, and identifying as an abnormal region each region formed by contiguous of those pixels which have values exceeding the predetermined threshold value.

13. The method according to claim 12, wherein said searching step comprises:

determining the size of each identified abnormal region and further identifying as an abnormal region only those previously identified possible abnormal regions which also exceed a predetermined size.

14. The method according to claim 12, wherein said searching step comprises:

determining which of said identified abnormal regions are in a boundary region of said difference image, and further identifying as abnormal regions only those previously identified possible abnormal regions also lying outside said boundary region.

15. The method according to claim 12, wherein said generating, correlating and searching steps are repeated to identify abnormal regions of said object derived from third and fourth digital images representing a different view of said object relative to said first and second digital images, and said searching step comprises:

determining which of said identified abnormal regions derived from said first and second digital images have spatial correspondence with identified abnormal regions derived from said third and fourth digital images, and further identifying as abnormal regions only those previously identified abnormal regions derived from said first and second digital images which have spatial correspondence with previously identified abnormal regions derived from said third and fourth digital images.

16. The method according to claim 13, wherein said searching step comprises:

determining which of said identified abnormal regions are in a boundary region of said difference image, and further identifying as abnormal regions only those previously identified abnormal regions also lying outside said boundary region.

17. The method according to claim 13, wherein said generating, correlating and searching steps are repeated to identify abnormal regions of said object derived from third and fourth digital images representing a different view of said object relative to said first and second digital images, and said searching step comprises:

determining which of said identified abnormal regions derived from said first and second digital images have spatial correspondence with identified abnormal regions derived from said third and fourth digital images, and further identifying as abnormal regions only those previously identified abnormal regions derived from said first and second digital images which also have spatial correspondence with previously identified abnormal regions derived from said third and fourth digital images.

18. The method according to claim 14, wherein said generating, correlating and searching steps are repeated to identify abnormal regions of said object derived from third and fourth digital images representing a different view of said object relative to said first and second digital views, and said searching step comprises:

determining which of said identified abnormal region derived from said first and second digital images have spatial correspondence with identified abnormal regions derived from said third and fourth digital images, and further identifying as abnormal regions only those previously identified abnormal regions derived from said first and second digital images which also have spatial correspondence with previously identified abnormal regions derived from said third and fourth digital images.

19. The method according to claim 16, wherein said generating, correlating and searching steps are repeated to identify abnormal regions of said object derived from third and fourth digital images representing a different view of said object relative to said first and second digital images, and said searching step comprises:

determining which of said identified abnormal regions derived from said first and second digital images have spatial correspondence with identified abnormal regions derived from said third and fourth digital images, and further identifying as an abnormal region only those previously identified abnormal regions derived from said first and second digital images which also have spatial correspondence with previously identified abnormal regions derived from said third and fourth digital images.

20. The method according to claim 11, wherein said searching step comprises:
 comparing the value of each pixel of said first runlength difference image with a predetermined threshold value, and
 identifying as an abnormal region each region formed by contiguous of those pixels which have values exceeding the predetermined threshold value.

21. The method according to claim 20, wherein said searching step comprises:
 determining the size of each identified abnormal region and further identifying as an abnormal region only those previously identified abnormal regions which exceed a predetermined size.

22. The method according to claim 20, wherein said searching step comprises:
 determining which of said identified abnormal regions are in a boundary region of said first runlength image, and
 further identifying as abnormal regions only those previously identified abnormal regions lying outside said boundary region.

23. The method according to claim 20, wherein said generating, correlating and searching steps are repeated to identify abnormal regions of said object derived from third and fourth digital images representing a different view of said object relative to said first and second digital images, and said searching step comprises:
 determining which of said identified abnormal regions derived from said first and second digital images have spatial correspondence with identified abnormal regions derived from said third and fourth digital images, and
 further identifying as abnormal regions only those previously identified abnormal regions derived from said first and second digital images which have spatial correspondence with previously identified abnormal regions derived from said third and fourth digital images.

24. The method according to claim 21, wherein said searching step comprises:
 determining which of said abnormal regions are in a boundary region of said first runlength image, and
 further identifying as abnormal regions only those previously identified abnormal regions also lying outside said boundary region.

25. The method according to claim 21, wherein said generating, correlating and searching steps are repeated to identify abnormal regions of said object derived from third and fourth digital images representing a different view of said object relative to said first and second digital images, and said searching step comprises:
 determining which of said identified abnormal regions derived from said first and second digital images have spatial correspondence with identified abnormal regions derived from said third and fourth digital images, and
 further identifying as abnormal regions only those previously identified abnormal regions derived from said first and second digital images which also have spatial correspondence with previously identified abnormal regions derived from said third and fourth digital images.

26. The method according to claim 22, wherein said generating, correlating and searching steps are repeated to identify abnormal regions of said object derived from third and fourth digital images representing a different view of said object relative to said first and second digital images, and said searching step comprises:
 determining which of said identified abnormal regions derived from said first and second digital images have spatial correspondence with identified abnormal regions derived from said third and fourth digital images, and
 further identifying as abnormal regions only those previously identified abnormal regions derived from said first and second digital images which also have spatial correspondence with previously identified abnormal region derived from said third and fourth digital images.

27. The method according to claim 24, wherein said generating, correlating and searching steps are repeated to identify abnormal regions of said object derived from third and fourth digital images representing a different view of said object relative to said first and second digital images, and said searching step comprises:
 determining which of said identified abnormal regions derived from said first and second digital images have spatial correspondence with identified abnormal regions derived from said third and fourth digital images, and
 further identifying as abnormal regions only those previously identified abnormal regions derived from said first and second digital images which also have spatial correspondence with previously identified abnormal regions derived from said third and fourth digital images.

28. The method according to claim 11, wherein said searching step comprises:
 comparing the value of each pixel of said second runlength image with a predetermined threshold value, and
 identifying as an abnormal region each region formed by contiguous of those pixels which have values exceeding the predetermined threshold.

29. The method according to claim 28, wherein said searching step comprises:
 determining the size of each identified abnormal region and further identifying as a abnormal region only those previously identified abnormal regions which exceed a predetermined size.

30. The method according to claim 28, wherein said searching step comprises:
 determining which of said identified abnormal regions are in a boundary region of said second runlength image, and further identifying as abnormal regions only those previously identified abnormal regions lying outside said boundary region.

31. The method according to claim 28, wherein said generating, correlating and searching steps are repeated to identify abnormal regions of said object derived from third and fourth digital images a representing different view of said object relative to said first and second digital images, and said searching step comprises:
 determining which of said identified abnormal regions derived from said first and second digital images have spatial correspondence with identified abnormal regions derived from said third and fourth digital images, and
 further identifying as abnormal regions only those previously identified abnormal regions derived from said first and second digital images which have spatial correspondence with previously identified abnormal regions derived from said third and fourth digital images.

32. The method according to claim 29, wherein said searching step comprises:
   determining which of said abnormal regions are in a boundary region of said second runlength image, and
   further identifying as abnormal regions only those previously identified abnormal regions also lying outside said boundary region.

33. The method according to claim 29, wherein said generating, correlating and searching steps are repeated to identify abnormal regions of said object derived from third and fourth digital images a representing different view of said object relative to said first and second digital images, and said searching step comprises:
   determining which of said identified abnormal regions derived from said first and second digital images have spatial correspondence with identified abnormal regions derived from said third and fourth digital images, and
   further identifying as abnormal regions only those previously identified abnormal regions derived from said first and second digital images which also have spatial correspondence with previously identified abnormal regions derived from said third and fourth digital images.

34. The method according to claim 30, wherein said generating, correlating and searching steps are repeated to identify abnormal regions of said object derived from third and fourth digital images representing a different view of said object relative to said first and second digital images, and said searching step comprises:
   determining which of said identified abnormal regions derived from said first and second digital images have spatial correspondence with identified abnormal regions derived from said third and fourth digital images, and
   further identifying as abnormal regions only those previously identified abnormal regions derived from said first and second digital images which also have spatial correspondence with previously identified abnormal regions derived from said third and fourth digital images.

35. The method according to claim 32, wherein said generating, correlating and searching steps are repeated to identify abnormal regions of said object derived from third and fourth digital images representing a different view of said object relative to said first and second digital images, and said searching step comprises:
   determining which of said identified abnormal regions derived from said first and second digital images have spatial correspondence with identified abnormal regions derived from said third and fourth digital images, and
   further identifying as abnormal regions only those previously identified abnormal regions derived from said first and second digital images which also have spatial correspondence with previously identified abnormal regions derived from said third and fourth digital images.

36. The method according to claim 1, comprising:
   aligning said digital images with respect to each other prior to performing said correlating step.

37. The method according to claim 2, wherein said indicating step comprises:
   indicating a center of said abnormal region.

38. The method according to claim 2, further comprising:
   classifying said abnormal region as being malignant or benign; and
   said indicating step comprising indicating a result of said classifying step.

39. The method according to claim 2, comprising:
   classifying said abnormal region as being malignant or benign, including
   determining a degree of spiculations of said abnormal region, and
   characterizing said abnormal region as being malignant or benign based on the determined degree of spiculations.

40. The method according to claim 39, wherein said step of determining a degree of spiculation of said abnormal region comprises:
   determining a center of said abnormal region,
   determining in at least one of said first and second digital images a range of amplitude values encompassing said abnormal region, and
   determining all contiguous pixels surrounding and contiguous with the center of said abnormal region and having a value within said range of amplitude values, said contiguous pixels thereby defining a grown image of said abnormal region.

41. The method according to claim 40, further comprising:
   determining the border of said grown image.

42. The method according to claim 39, wherein said classifying step further comprises:
   determining a border of said abnormal region,
   smoothing spatial locations of said border of said abnormal region to produce a smoothed border,
   determining a difference between said border of said abnormal region and said smoothed border,
   determining an RMS variation and a first moment of power spectrum of the difference between said border of said abnormal region and said smoothed border, and
   characterizing said abnormal region as malignant or benign based on the relationship of the RMS variation and first moment of power spectrum.

43. The method according to claim 39, wherein said classifying step comprises:
   blurring of said abnormal region to define a blurred region,
   determining the area of said abnormal region and the area of said blurred region,
   determining a difference between the area of said abnormal region and the area of said blurred region, and
   characterizing said abnormal region as malignant or benign based on the difference between said areas.

44. The method according to claim 39, wherein said classifying step comprises:
   determining a border of said abnormal region,
   blurring of said abnormal region by spatial filtering to define a blurred region,
   determining a border of said blurred region,
   determining a difference between said border of said abnormal region and said border of said blurred region,
   determining an RMS variation and a first moment of power spectrum of the difference between said border of said abnormal region and said border of said blurred region, and
   characterizing said abnormal region as malignant or benign based on the relationship of the RMS variation and the first moment of power spectrum.

45. The method according to claim 39, wherein said classifying step comprises:
blurring of said abnormal region by spatial filtering to define a blurred region,
determining a first discrete Fourier transform of said abnormal region and a second discrete Fourier transform of said blurred region,
determining a difference between spectra of the first and second discrete Fourier transforms,
determining an RMS variation and a first moment of a power spectrum of said difference between spectra, and
characterizing said abnormal region as malignant or benign based on the relationship of the RMS variation and the first moment of power spectrum.

46. A method for automated classification of an abnormal region in the form of a lesion or a parenchymal distortion in a digital image of an object, comprising:
determining a degree of spiculations in said abnormal region; and
characterizing said abnormal region as being malignant or benign based on the determined degree of spiculations.

47. The method according to claim 46, wherein said step of determining a degree of spiculations of said abnormal region comprises:
determining a center of said abnormal region,
determining in said digital image a range of amplitude values encompassing said abnormal region, and
determining all contiguous pixels surrounding and contiguous with the center of said abnormal region and having a value within said range of amplitude values, said contiguous pixels thereby defining a grown image of said abnormal region.

48. The method according to claim 47, further comprising:
determining the border of said grown image.

49. The method according to claim 46, wherein:
said step of determining a degree of spiculations comprises,
determining a border of said abnormal region,
smoothing spatial locations of said border of said abnormal region to produce a smoothed border,
determining a difference between said border of said abnormal region and said smoothed border, and
determining an RMS variation and a first moment of power spectrum of the difference between said border of said abnormal region and said smoothed border; and
said characterizing step comprises, characterizing said abnormal region as malignant or benign based on the relationship of the RMS variation and first moment of power spectrum.

50. The method according to claim 46, wherein:
said step of determining a degree of spiculations comprises,
blurring of said abnormal region to define a blurred region,
determining the area of said abnormal region and the area of said blurred region, and
determining a difference between the area of said abnormal region and the area of said blurred region; and
said characterizing step comprises,
characterizing said abnormal region as malignant or benign based on the difference between said areas.

51. The method according to claim 46, wherein:
said step of determining a degree of spiculations comprises,
determining a border of said abnormal region,
blurring of said abnormal region by spatial filtering to define a blurred region,
determining a border of said blurred region,
determining a difference between said border of said abnormal region and said border of said blurred region, and determining an RMS variation and a first moment of power spectrum of the difference between said border of said abnormal region and said border of said blurred region; and
said characterizing step comprises,
characterizing said abnormal region as malignant or benign based on the relationship of the RMS variation and the first moment of power spectrum.

52. The method according to claim 46, wherein said step of determining a degree of spiculations comprises,
blurring of said abnormal region by spatial filtering to define a blurred region,
determining a first discrete Fourier transform of said abnormal region and a second discrete Fourier transform of said blurred region,
determining a difference between spectra of the first and second discrete Fourier transforms, and
determining an RMS variation and first moment of a power spectrum of said difference between spectra; and
said characterizing steps comprises,
characterizing said abnormal region as malignant or benign base on the relationship of the RMS variation and the first moment of power spectrum.

53. A method of processing at least first and second digital images represented by at least first and second digital data, respectively, of at least one selected portion of an object, comprising:
determining at least first and second histograms of respective of said at least first and second digital images;
determining at least first and second cumulative histograms of said at least first and second histograms, respectively; and
matching at least the second cumulative histogram to the first cumulative histogram by modifying at least said second digital data based on a predetermined relationship between the data of the a least first and second cumulative histograms.

54. The method according to claim 53, wherein said at least first and second cumulative histograms each have a first axis defining data values and a second axis defining a total percent of pixels having data values equal to or less than a respective data value on said first axis, and said matching step comprises:
determining for each data value on the first axis of said second cumulative histogram a respective percent of pixels on the second axis of said second cumulative histogram,
determining for each respective percent determined in the preceding step a respective data value corresponding thereto on the first axis of the first cumulative histogram, and
converting the data value of each pixel having a data value at a particular percent in said second cumulative histogram to the respective data value at the same particular percent in said first cumulative histogram determined in said preceding determining step.

55. A system for automated analysis of abnormalities in the form of lesions and parenchymal distortions using digital images, comprising:

means for generating at least first and second image data from respective of at least first and second digital images derived from at least one selected portion of an object; and means for correlating said at least first and second image data to produce correlated data in which normal anatomical structured background is removed.

56. The system according to claim 55, further comprising:

means for searching said correlated data using at least one predetermined criterion to identify in at least one of said digital images an abnormal region represented by a portion of said correlated data which meets said predetermined criterion; and means for indicating the location of said abnormal region in said at least one of said digital images.

57. The system according to claim 56, wherein said means for generating comprises:

means for determining at least first and second histograms of respective of said at least first and second digital images, means for determining at least first and second cumulative histograms of said at least first and second histograms, respectively, and means for matching at least the second cumulative histogram to the first cumulative histogram by modifying data values of pixels of at least the second digital image based on a predetermined relationship between the data of the at least first and second cumulative histograms, said second image data corresponding to modified pixel values of said second digital image and said first image data corresponding to pixel values of the first digital image.

58. The system according to claim 57, wherein said generating comprises:

means for determining N at least first and second threshold values, and means for determining N at least first and second threshold images for each of said at least first and second digital images by comparing each pixel of said at least first and second digital images with each of respective of said N at least first and second threshold values and assigning each said pixel a first predetermined value when said pixel is above the threshold value and a second predetermined value when said pixel is below the threshold value, said first image data being N image data corresponding to the N first threshold images and said second image data being N image data corresponding to the N second threshold images.

59. The system according to claim 58, wherein said means for determining said N at least first and second threshold images comprises:

means for assigning to each said pixel of said at least first and second digital images a predetermined first constant value or a predetermined second constant value when that pixel has a value above or below said threshold value, respectively.

60. The system according to claim 58, wherein said means for determining said N at least first and second threshold images comprises:

means for assigning each said pixel of said at least first and second digital images the value of that pixel in the respective digital image when that pixel has a value above said threshold value, and means for assigning each said pixel of said at least first and second digital images a predetermined constant value when that pixel has a value below said threshold value.

61. The system according to claim 58, wherein said means for determining said N at least first and second threshold values comprises:

means for determining at least first and second histograms of said at least first and second digital images, respectively, and means for defining said N at least first and second threshold values as being the pixel values at selected percentages of said at least first and second histograms, respectively.

62. The system according to claim 55, wherein said means for correlating comprises:

means for forming a difference image based on the difference between said first and second image data.

63. The system according to claim 57, wherein said means for correlating comprises:

means for forming a difference image based on the difference between said first and second image data.

64. The system according to claim 58, wherein said means for correlating comprises:

means for forming N difference images based on the difference between the N first threshold images and respective of the N second threshold images.

65. The system according to claim 64, wherein said means for correlating comprises:

means for forming a first runlength image in which each pixel of the first runlength image corresponds to an identical pixel location in said N difference images and is assigned a value in dependence on the largest number of said identical pixels which in consecutive order of said N difference images have a predetermined positive value, and means for forming a second runlength image in which each pixel of the second runlength image corresponds to an identical pixel location in said N images and is assigned a value in dependence on the largest number of said identical pixels which in consecutive order of said N difference images have a predetermined negative value.

66. The system according to claim 63, wherein said means for searching comprises:

means for comparing the value of each pixel of said difference image with a predetermined threshold value, and means for identifying as an abnormal region each region formed by contiguous of those pixels which have values exceeding the predetermined threshold value.

67. The system according to claim 66, wherein said means for searching comprises:

means for determining the size of each identified abnormal region and further identifying as an abnormal region only those previously identified possible abnormal regions which also exceed a predetermined size.

68. The system according to claim 66, wherein said means for searching comprises:

means for determining which of said identified abnormal regions are in a boundary region of said difference image, and means for further identifying as abnormal regions only those previously identified possible abnormal regions also lying outside said boundary region.

69. The system according to claim 66, wherein abnormal regions of said object derived from third and fourth digital images representing a different view of said object relative to said first and second digital images are identified, and said means for searching comprises:
- means for determining which of said identified abnormal regions derived from said first and second digital images have spatial correspondence with identified abnormal regions derived from said third and fourth digital images, and
- means for further identifying as abnormal regions only those previously identified abnormal regions derived from said first and second digital images which have spatial correspondence with previously identified abnormal regions derived from said third and fourth digital images.

70. The system according to claim 67, wherein said means for searching comprises:
- means for determining which of said identified abnormal regions are in a boundary region of said difference image, and
- means for further identifying as abnormal regions only those previously identified abnormal regions also lying outside said boundary region.

71. The system according to claim 67, wherein abnormal regions of said object derived from third and fourth digital images representing a different view of said object relative to said first and second digital images are identified, and said means for searching comprises:
- means for determining which of said identified abnormal regions derived from said first and second digital images have spatial correspondence with identified abnormal regions derived from said third and fourth digital images, and
- means for further identifying as abnormal regions only those previously identified abnormal regions derived from said first and second digital images which also have spatial correspondence with previously identified abnormal regions derived from said third and fourth digital images.

72. The system according to claim 68, wherein abnormal regions of said object derived from third and fourth digital images representing a different view of said object relative to said first and second digital views are identified, and said means for searching comprises:
- means for determining which of said identified abnormal regions derived from said first and second digital images have spatial correspondence with identified abnormal regions derived from said third and fourth digital images, and
- means for further identifying as abnormal regions only those previously identified abnormal regions derived from said first and second digital images which also have spatial correspondence with previously identified abnormal regions derived from said third and fourth digital images.

73. The system according to claim 70, wherein abnormal regions of said object derived from third and fourth digital images representing a different view of said object relative to said first and second digital images are identified, and said means for searching comprises:
- means for determining which of said identified abnormal regions derived from said first and second digital images have spatial correspondence with identified abnormal regions derived from said third and fourth digital images, and
- means for further identifying as an abnormal region only those previously identified abnormal regions derived from said first and second digital images which also have spatial correspondence with previously identified abnormal regions derived from said third and fourth digital images.

74. The system according to claim 68, wherein said means for searching comprises:
- means for comparing the value of each pixel of said first runlength difference image with a predetermined threshold value, and
- means for identifying as an abnormal region each region formed by contiguous of those pixels which have values exceeding the predetermined threshold value.

75. The system according to claim 74, wherein said means for searching comprises:
- means for determining the size of each identified abnormal region and further identifying as an abnormal region only those previously identified abnormal regions which exceed a predetermined size.

76. The system according to claim 74, wherein said means for searching comprises:
- means for determining which of said identified abnormal regions are in a boundary region of said first runlength image, and
- means for further identifying as abnormal regions only those previously identified abnormal regions lying outside said boundary region.

77. The system according to claim 74, wherein abnormal regions of said object derived from third and fourth digital images representing a different view of said object relative to said first and second digital images are identified, and said means for searching comprises:
- means for determining which of said identified abnormal regions derived from said first and second digital images have spatial correspondence with identified abnormal regions derived from said third and fourth digital images, and
- means for further identifying as abnormal regions only those previously identified abnormal regions derived from said first and second digital images which have spatial correspondence with previously identified abnormal regions derived from said third and fourth digital images.

78. The system according to claim 75, wherein said means for searching comprises:
- means for determining which of said abnormal regions are in a boundary region of said first runlength image, and
- means for further identifying as abnormal regions only those previously identified abnormal regions also lying outside said boundary region.

79. The system according to claim 75, wherein abnormal regions of said object derived from third and fourth digital images representing a different view of said object relative to said first and second digital images are identified, and said means for searching comprises:
- means for determining which of said identified abnormal regions derived from said first and second digital images have spatial correspondence with identified abnormal regions derived from said third and fourth digital images, and
- means for further identifying as abnormal regions only those previously identified abnormal regions derived from said first and second digital images which also have spatial correspondence with previously identified abnormal regions derived from said third and fourth digital images.

80. The system according to claim 76, wherein abnormal regions of said object derived from third and fourth digital images representing a different view of said object relative to said first and second digital images are identified, and said means for searching comprises:
   means for determining which of said identified abnormal regions derived from said first and second digital images have spatial correspondence with identified abnormal regions derived from said third and fourth digital images, and
   means for further identifying as abnormal regions only those previously identified abnormal regions derived from said first and second digital images which also have spatial correspondence with previously identified abnormal region derived from said third and fourth digital images.

81. The system according to claim 78, wherein abnormal regions of said object derived from third and fourth digital images representing a different view of said object relative to said first and second digital images are identified, and said means for searching comprises:
   means for determining which of said identified abnormal regions derived from said first and second digital images have spatial correspondence with identified abnormal regions derived from said third and fourth digital images, and
   means for further identifying as abnormal regions only those previously identified abnormal regions derived from said first and second digital images which also have spatial correspondence with previously identified abnormal regions derived from said third and fourth digital images.

82. The system according to claim 65, wherein said means for searching comprises:
   means for comparing the value of each pixel of said second runlength image with a predetermined threshold value, and
   means for identifying as an abnormal region each region formed by contiguous of those pixels which have values exceeding the predetermined threshold.

83. The system according to claim 82, wherein said means for searching comprises:
   means for determining the size of each identified abnormal region and further identifying as a abnormal region only those previously identified abnormal regions which exceed a predetermined size.

84. The system according to claim 82, wherein said means for searching comprises:
   determining which of said identified abnormal regions are in a boundary region of said second runlength image, and
   means for further identifying as abnormal regions only those previously identified abnormal regions lying outside said boundary region.

85. The system according to claim 82, wherein abnormal regions of said object derived from third and fourth digital images representing a different view of said object relative to said first and second digital images are identified, and said means for searching comprises:
   means for determining which of said identified abnormal regions derived from said first and second digital images have spatial correspondence with identified abnormal regions derived from said third and fourth digital images, and
   means for further identifying as abnormal regions only those previously identified abnormal regions derived from said first and second digital images which have spatial correspondence with previously identified abnormal regions derived from said third and fourth digital images.

86. The system according to claim 83, wherein said means for searching comprises:
   means for determining which of said abnormal regions are in a boundary region of said second runlength image, and
   means for further identifying as abnormal regions only those previously identified abnormal regions also lying outside said boundary region.

87. The system according to claim 83, wherein abnormal regions of said object derived from third and fourth digital images representing a different view of said object relative to said first and second digital images are identified, and said means for searching comprises:
   means for determining which of said identified abnormal regions derived from said first and second digital images have spatial correspondence with identified abnormal regions derived from said third and fourth digital images, and
   means for further identifying as abnormal regions only those previously identified abnormal regions derived from said first and second digital images which also have spatial correspondence with previously identified abnormal regions derived from said third and fourth digital images.

88. The system according to claim 84, wherein abnormal regions of said object derived from third and fourth digital images representing a different view of said object relative to said first and second digital images are identified, and said means for searching comprises:
   means for determining which of said identified abnormal regions derived from said first and second digital images have spatial correspondence with identified abnormal regions derived from said third and fourth digital images, and
   means for further identifying as abnormal regions only those previously identified abnormal regions derived from said first and second digital images which also have spatial correspondence with previously identified abnormal regions derived from said third and fourth digital images.

89. The system according to claim 86, wherein abnormal regions of said object derived from third and fourth digital images representing a different view of said object relative to said first and second digital images are identified, and said means for searching further comprises:
   means for determining which of said identified abnormal regions derived from said first and second digital images have spatial correspondence with identified abnormal regions derived from said third and fourth digital images, and
   means for further identifying as abnormal regions only those previously identified abnormal regions derived from said first and second digital images which also have spatial correspondence with previously identified abnormal regions derived from said third and fourth digital images.

90. The system according to claim 55, comprising:
   means for aligning said digital images with respect to each other.

91. The system according to claim 56, wherein said means for indicating comprises:
means for indicating a center of said abnormal region.

92. The system according to claim 57, further comprising:
means for classifying said abnormal region as being malignant or benign; and
said means for indicating comprising means for indicating a result of said classifying step 93. The system according to claim 56, comprising:
means for classifying said abnormal region as being malignant or benign, including
means for determining a degree of spiculations of said abnormal region, and
means for characterizing said abnormal region as being malignant or benign based on the determined degree of spiculations.

94. The system according to claim 93, wherein said means for determining a degree of spiculation of said abnormal region comprises:
means for determining a center of said abnormal region,
means for determining in at least one of said first and second digital images a range of amplitude values encompassing said abnormal region, and
means for determining all contiguous pixels surrounding and contiguous with the center of said abnormal region and having a value within said range of amplitude values, said contiguous pixels thereby defining a grown image of said abnormal region.

95. The system according to claim 94, further comprising:
means for determining the border of said grown image.

96. The system according to claim 93, wherein said means for classifying further comprises:
means for determining a border of said abnormal region,
means for smoothing spatial locations of said border of said abnormal region to produce a smoothed border,
means for determining a difference between said border of said abnormal region and said smoothed border,
means for determining an RMS variation and a first moment of power spectrum of the difference between said border of said abnormal region and said smoothed border, and
means for characterizing said abnormal region as malignant or benign based on the relationship of the RMS variation and first moment of power spectrum.

97. The system according to claim 93, wherein said means for classifying comprises:
means for blurring of said abnormal region to define a blurred region,
means for determining the area of said abnormal region and the area of said blurred region,
means for determining a difference between the area of said abnormal region and the area of said blurred region, and
means for characterizing said abnormal region as malignant or benign based on the difference between said areas.

98. The system according to claim 93, wherein said means for classifying comprises:
means for determining a border of said abnormal region,
means for blurring of said abnormal region by spatial filtering to define a blurred region,
means for determining a border of said blurred region,
means for determining a difference between said border of said abnormal region and said border of said blurred region,
means for determining an RMS variation and a first moment of power spectrum of the difference between said border of said abnormal region and said border of said blurred region, and
means for characterizing said abnormal region as malignant or benign based on the relationship of the RMS variation and the first moment of power spectrum.

99. The system according to claim 93, wherein said means for classifying comprises:
means for blurring of said abnormal region by spatial filtering to define a blurred region,
means for determining a first discrete Fourier transform of said abnormal region and a second discrete Fourier transform of said blurred region,
means for determining a difference between spectra of the first and second discrete Fourier transforms,
means for determining an RMS variation and a first moment of a power spectrum of said difference between spectra, and
means for characterizing said abnormal region as malignant or benign based on the relationship of the RMS variation and the first moment of power spectrum.

100. A system for automated classification of an abnormal region in the form of a lesion or a parenchymal distortion in a digital image of an object, comprising:
means for determining a degree of spiculations in said abnormal region; and
means for characterizing said abnormal region as being malignant or benign based on the determined degree of spiculations.

101. The system according to claim 100, wherein said means for determining a degree of spiculations of said abnormal region comprises:
means for determining a center of said abnormal region,
means for determining in said digital image a range of amplitude values encompassing said abnormal region, and
means for determining all contiguous pixels surrounding and contiguous with the center of said abnormal region and having a value within said range of amplitude values, said contiguous pixels thereby defining a grown image of said abnormal region.

102. The system according to claim 101, further comprising:
means for determining the border of said grown image.

103. The system according to claim 100, wherein:
said means for determining a degree of spiculations comprises,
means for determining a border of said abnormal region,
means for smoothing spatial locations of said border of said abnormal region to produce a smoothed border, and
means for determining a difference between said border of said abnormal region and said smoothed border, and means for determining an RMS variation and a first moment of power spectrum of the difference between said border of said abnormal region and said smoothed border; and said means for characterizing comprises, means for characterizing said abnormal region as malignant or benign based on the relationship of the RMS variation and first moment of power spectrum.

104. The system according to claim 100, wherein:

said means for determining a degree of spiculations comprises, means for blurring of said abnormal region to define a blurred region, means for determining the area of said abnormal region and the area of said blurred region, and means for determining a difference between the area of said abnormal region and the area of said blurred region; and said means for characterizing comprises, means for characterizing said abnormal region as malignant or benign based on the difference between said areas.

105. The system according to claim 100, wherein:

said means for determining a degree of spiculations comprises, means for determining a border of said abnormal region, means for blurring of said abnormal region by spatial filtering to define a blurred region, means for determining a border of said blurred region, means for determining a difference between said border of said abnormal region and said border of said blurred region, and means for determining an RMS variation and a first moment of power spectrum of the difference between said border of said abnormal region and said border of said blurred region; and said means for characterizing comprises, means for characterizing said abnormal region as malignant or benign based on the relationship of the RMS variation and the first moment of power spectrum.

106. The system according to claim 100, wherein said means for determining a degree of spiculations comprises, means for blurring of said abnormal region by spatial filtering to define a blurred region, means for determining a first discrete Fourier transform of said abnormal region and a second discrete Fourier transform of said blurred region, means for determining a difference between spectra of the first and second discrete Fourier transforms. and means for determining an RMS variation and first moment of a power spectrum of said difference between spectra; and said means for characterizing comprises, means for characterizing said abnormal region as malignant or benign based on the relationship of the RMS variation and the first moment of power spectrum.

107. A system for processing at least first and second digital images represented by at least first and second digital data, respectively, of at least one selected portion of an object, comprising:

means for determining at least first and second histograms of respective of said at least first and second digital images;

means for determining at least first and second cumulative histograms of said at least first and second histograms, respectively; and means for matching at least he second cumulative histogram to the first cumulative histogram by modifying at least said second digital data based on a predetermined relationship between the data of the at least first and second cumulative histograms.

108. The system according to claim 107, wherein said at least first and second cumulative histograms each have a first axis defining data values and a second axis defining a total percent of pixels having data values equal to or less than a respective data value on said first axis, and said means for matching comprises:

first means for determining for each data value on the first axis of said second cumulative histogram a respective percent of pixels on the second axis of said second cumulative histogram, second means for determining for each respective percent determined by said first means a respective data value corresponding thereto on the first axis of the first cumulative histogram, and means for converting the data value of each pixel having a data value at a particular percent in said second cumulative histogram to the respective data value at the same particular percent in said first cumulative histogram determined by said second determining means.

* * * * *